US006602902B2

(12) United States Patent
Shashoua et al.

(10) Patent No.: US 6,602,902 B2
(45) Date of Patent: *Aug. 5, 2003

(54) DHA-PHARMACEUTICAL AGENT CONJUGATES TO IMPROVE TISSUE SELECTIVITY

(75) Inventors: Victor E. Shashoua, Brookline, MA (US); Charles E. Swindell, Merion, PA (US); Nigel L. Webb, Bryn Mawr, PA (US); Matthews O. Bradley, Layton, PA (US)

(73) Assignee: Protarga, Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/846,838

(22) Filed: May 1, 2001

(65) Prior Publication Data

US 2002/0010208 A1 Jan. 24, 2002

Related U.S. Application Data

(63) Continuation of application No. 09/135,291, filed on Aug. 17, 1998, now abandoned, which is a continuation of application No. 08/651,312, filed on May 22, 1996, now Pat. No. 5,795,909.

(51) Int. Cl.[7] .......................... A61K 35/60; A61K 31/56; A61K 31/23; A61K 31/202
(52) U.S. Cl. ..................... 514/449; 514/169; 514/549; 514/552; 514/558; 514/560; 424/523
(58) Field of Search ................. 514/449, 169, 514/549, 552, 558, 560; 424/523

(56) References Cited

U.S. PATENT DOCUMENTS

| | | | |
|---|---|---|---|
| 4,088,646 A | 5/1978 | Ishida et al. |
| 4,185,095 A | 1/1980 | Young |
| 4,287,184 A | 9/1981 | Young |
| 4,407,744 A | 10/1983 | Young |
| 4,636,494 A | 1/1987 | Growden et al. |
| 4,692,441 A | 9/1987 | Alexander et al. |
| 4,704,393 A | 11/1987 | Wakabayashi et al. |
| 4,729,989 A | 3/1988 | Alexander |
| 4,788,063 A | 11/1988 | Fisher et al. |
| 4,814,470 A | 3/1989 | Colin et al. |
| 4,857,653 A | 8/1989 | Colin et al. |
| 4,943,579 A | 7/1990 | Vishnuvajjala et al. |
| 4,968,672 A | 11/1990 | Jacobson et al. |
| 5,068,224 A | 11/1991 | Fryklund et al. |
| 5,112,596 A | 5/1992 | Malfroy-Camine |
| 5,112,863 A | 5/1992 | Hashimoto et al. |
| 5,116,624 A | 5/1992 | Horrobin et al. |
| 5,120,760 A | 6/1992 | Horrobin |
| 5,141,958 A | 8/1992 | Crozier-Willi et al. |
| 5,169,764 A | 12/1992 | Shooter et al. |
| 5,194,654 A | 3/1993 | Hostetler et al. |
| 5,214,062 A | 5/1993 | Mark et al. |
| 5,216,023 A | 6/1993 | Literati-Nagu et al. |
| 5,216,142 A | 6/1993 | Horrobin et al. |
| 5,223,263 A | 6/1993 | Hostetler et al. |
| 5,246,726 A | 9/1993 | Horrobin et al. |
| 5,250,722 A | 10/1993 | Bombardelli et al. |
| 5,276,020 A | 1/1994 | Horrobin et al. |
| 5,284,876 A | 2/1994 | Shashoua et al. |
| 5,308,832 A | 5/1994 | Garleb et al. |
| 5,314,991 A | 5/1994 | Oka et al. |
| 5,336,684 A | 8/1994 | Murray et al. |
| 5,352,596 A | 10/1994 | Cheung et al. |
| 5,356,928 A | 10/1994 | Murray et al. |
| 5,362,831 A | 11/1994 | Mongelli et al. |
| 5,411,947 A | 5/1995 | Hostetler et al. |
| 5,420,276 A | 5/1995 | Norbeck |
| 5,447,936 A | 9/1995 | Hausheer et al. |
| 5,453,520 A | 9/1995 | Bombardelli et al. |
| 5,459,256 A | 10/1995 | Marquez et al. |
| 5,466,841 A | 11/1995 | Horrobin et al. |
| 5,468,754 A | 11/1995 | Hausheer et al. |
| 5,473,055 A | 12/1995 | Mongelli et al. |

(List continued on next page.)

FOREIGN PATENT DOCUMENTS

| | | |
|---|---|---|
| DE | 2602175 A1 | 7/1976 |
| DE | 422 4737 A1 | 2/1994 |
| EP | 0 030 009 A1 | 6/1981 |
| EP | 0 350 287 | 10/1990 |
| EP | 0 615 752 A1 | 9/1994 |
| EP | 0 693 498 A1 | 1/1996 |
| FR | 2 698 269 A | 8/1997 |
| JP | 76-9469 A | 1/1975 |
| JP | 75-427/1983 A | 4/1983 |
| JP | 59025327 A | 2/1984 |

(List continued on next page.)

OTHER PUBLICATIONS

Chen, et al. "Taxol Structure–Activity Relationships: Synthesis and Biological Evaluation of Taxol Analogs Modified at C–7," *Bioorganic & Medicinal Chemistry Letters*, vol. 4, No. 18, pp. 2223–2228, 1994.

De Groot, et al., "Synthesis and Biological Evaluation of 2'–Carbamate–Linked and 2'–Carbonate–Linked Prodrugs of Paclitaxel: Selective Activation by the Tumor–Associated Protease Plasmin," *J. Med. Chem.*, 2000, vol. 43, pp. 3093–3102.

Dischino, et al., "Synthesis of Monosodium Salt of Carbon–14 Labeled Paclitaxel (Taxol ®) 2'–Ethyl Carbonate 7–Phophonooxymethyl Ether, a Potential Prodrug of Paclitaxel," *Journal of Labelled Compounds and Radiopharmaceuticals*, vol. XXXIX, No. 2.

(List continued on next page.)

*Primary Examiner*—Frederick Krass
*Assistant Examiner*—Donna Jagoe
(74) *Attorney, Agent, or Firm*—Wolf, Greenfield, & Sacks, P.C.

(57) ABSTRACT

The invention provides conjugates of cis-docosahexaenoic acid and pharmaceutical agents useful in treating noncentral nervous system conditions. Methods for selectively targeting pharmaceutical agents to desired tissues are provided.

8 Claims, 14 Drawing Sheets

U.S. PATENT DOCUMENTS

| | | | |
|---|---|---|---|
| 5,476,954 A | | 12/1995 | Bourzat et al. |
| 5,484,809 A | | 1/1996 | Hostetler et al. |
| 5,494,999 A | | 2/1996 | Hale et al. |
| 5,496,714 A | | 3/1996 | Comb et al. |
| 5,504,102 A | | 4/1996 | Agharkar et al. |
| 5,516,800 A | | 5/1996 | Horrobin |
| 5,580,556 A | | 12/1996 | Horrobin |
| 5,580,899 A | | 12/1996 | Mayhew et al. |
| 5,597,719 A | | 1/1997 | Freed et al. |
| 5,604,216 A | | 2/1997 | Horrobin |
| 5,654,290 A | | 8/1997 | Bayon et al. |
| 5,716,614 A | | 2/1998 | Katz et al. |
| 5,750,572 A | | 5/1998 | Bruzzese |
| 5,795,909 A | * | 8/1998 | Shashoua et al. ........... 514/449 |
| 5,814,456 A | | 9/1998 | O'Rand et al. |
| 5,919,815 A | * | 7/1999 | Bradley et al. ............. 514/449 |
| 5,922,695 A | | 7/1999 | Arimilli et al. |
| 5,925,669 A | * | 7/1999 | Katz et al. .................. 514/449 |
| 5,977,061 A | | 11/1999 | Holy et al. |
| 5,977,089 A | | 11/1999 | Arimilli et al. |
| 5,977,174 A | | 11/1999 | Bradley et al. |
| 5,985,854 A | | 11/1999 | Kozak |
| 5,994,392 A | | 11/1999 | Shashoua |
| 6,043,230 A | | 3/2000 | Arimilli et al. |
| 6,069,249 A | | 5/2000 | Arimilli et al. |
| 6,077,837 A | | 6/2000 | Kozak |
| 6,080,877 A | | 6/2000 | Swindell et al. |
| 6,136,796 A | | 10/2000 | Kozak |
| 6,153,653 A | | 11/2000 | Shashoua |
| 6,166,089 A | | 12/2000 | Kozak |
| 6,197,764 B1 | | 3/2001 | Bradley et al. |
| 6,225,444 B1 | | 5/2001 | Shashoua |
| 6,225,460 B1 | | 5/2001 | Bischofberger et al. |
| 6,252,060 B1 | | 6/2001 | Hostetler |
| 6,258,836 B1 | | 7/2001 | Shashoua |
| 6,281,376 B1 | | 8/2001 | Whittaker et al. |
| 6,291,690 B1 | | 9/2001 | Mayhew et al. |
| 2001/0000692 A1 | | 5/2001 | Myhren et al. |

FOREIGN PATENT DOCUMENTS

| | | | |
|---|---|---|---|
| JP | 59-204175 A2 | 11/1984 | |
| JP | 1153629 A | 6/1989 | |
| JP | 1203331 A | 8/1989 | |
| JP | 1287022 A | 11/1989 | |
| JP | 6016548 A | 1/1994 | |
| JP | 8027010 A | 1/1996 | |
| JP | 815133 A | 6/1996 | |
| JP | 8163991 A | 6/1996 | |
| JP | 9025231 A | 1/1997 | |
| JP | 9030963 A | 2/1997 | |
| WO | WO 89/02733 | 4/1989 | |
| WO | WO 90/00555 | 1/1990 | |
| WO | WO 92/16554 A1 | 10/1992 | |
| WO | WO 92/20362 A1 | 11/1992 | |
| WO | WO 93/00910 | 1/1993 | |
| WO | WO 93/11668 A1 | 6/1993 | |
| WO | WO 94/07880 A1 | 4/1994 | |
| WO | WO 94/11547 A1 | 5/1994 | |
| WO | WO 94/12530 A1 | 6/1994 | |
| WO | WO 94/13654 A1 | 6/1994 | |
| WO | WO 94/22887 A1 | 10/1994 | |
| WO | WO 94/24107 A1 | 10/1994 | |
| WO | WO 95/01969 A1 | 1/1995 | |
| WO | WO 95/13270 A1 | 5/1995 | |
| WO | WO 95/13271 A1 | 5/1995 | |
| WO | WO 95/33736 A1 | 12/1995 | |
| WO | WO 96/01259 A1 | 1/1996 | |
| WO | WO 96/12696 A1 | 5/1996 | |
| WO | WO 96/27380 A1 | 9/1996 | |
| WO | WO 97/44026 A1 | 11/1997 | |
| WO | WO 97/44063 A3 | 11/1997 | |
| WO | WO 97/44336 A1 | 11/1997 | |
| WO | WO 98/21223 | 5/1998 | |
| WO | WO 98/32718 | 7/1998 | |
| WO | WO 99/52887 A1 | 10/1999 | |
| ZA | 9603433 A | 10/1996 | |

OTHER PUBLICATIONS

Greenwald, et al., Highly Water Soluble Taxol Derivatives: 7–Polyethylene Glycol Carbamates and Carbonates, *J. Org. Chem.*, 1995, vol. 60, pp. 331–336.

Halmos, et al. "Fatty Acid Conjugates of 2'–Deoxy–5'–Fluororidine as Prodrugs for the Selective Delivery of 5–Fluorouracil to Tumor Cells" *Biochemical Pharmacology*, (1992) 44:1:149–155.

Hong et al., "Nucleoside–ether lipid conjugates as biotransformed prodrugs of antitumor and antiviral nucleosides" *Journal of Lipid Mediators and Cell Signalling.* 10: 159–161 (1994).

Karmali, R., "N–3 Fatty Acids: Biochemical Actions In Cancer", *J. Nutr. Sci. Vitaminol. (Tokyo)*, (1992), 148–152. (Abstract).

Minami, M., et al., "Effects Of Low–Dose Eicosapentaenoic Acid, Docosahexaenoic Acid And Dietary Fat On The Incidence, Growth And Cell Kinetics Of Mammary Carcinomas In Rats", *Oncology*, (1996), 53(5):398–405.

UEDA et al., "Synthesis and Antitumor Evaluation of 2'–Oxycarbonylpaclitaxels (Paclitaxel02'–Carbonates)", *Bioorganic & Medicinal Chemistry Letters*, vol. 4, No. 15, pp. 1861–1864, 1994.

Ansari et al., "Fatty acid conjugates of xenobiotics," *Taxicol. Lett.* (1995), 75, 1–17.

Pouillart, "Role of butyric acid and its derivatives in the treatment of colorectal cancer and homoglobinopathics," *Life Sci.* (1998), 63(20), 1739–1760.

Anel, A., et al., "Increased Cytotoxicity Of Polyunsaturated Fatty Acids On Human Tumoral B And And T–Cell Lines Compared With Normal Lymphocytes", *Leukemia*, (1992), 6(7):680–688.

Anel, B., et al. "Cytotoxicity Of Chlorambucil And Chlorambucil–Fatty Acid Conjugates Against Human Lymphomas And Normal Peripheral Blood Lymphocytes", *Biochem Pharmacol*, (1990), 40(6):1193–1200.

Begin, M.E., et al., "Differential Killing Of Human Carcinoma Cells Supplemented With N–3 And N–6 Polyunsaturated Fatty Acids", *J Natl Cancer Inst*, (1986), 77(5):1053–1062. (Abstract).

Bourat, et al., "Long Chain Esters of Pipotiazine as Long-Acting Psychotropic Pro–Drug", *Med. Chem. Proc. Int. Symp.* 5th (1976) pp. 105–114.

Braam, J., et al., *Cell*, 60 357–364 (1990).

Burns, C.P., et al., "Effect Of Docosahexaenoic Acid On Rate Of Differentiation Of H1–60 Human Leukemia", *Cancer Res*, (1989), 49:3252–3258.

Carboni et al., "Synthesis of a Photoaffinity Analog of Taxol as an Approach to Identify the Taxol Binding Site on Microtubules", *Journal of Medicinal Chem.* (Sep. 8, 1992).

Chajes, V., et al., "Influence Of N–3 Fatty Acids On The Growth Of Human Breast Cancer Cells In Vitro: Relationship To Peroxides And Vitamin–E", *Breast Cancer Res Treat*, (1995), 34:199–212.

de Antueno, R.J., et al., "In Vitro Effect Of Eicosapentaenoic And Docosahexaenoic Acids On Prostaglandin E2 Synthesis In A Human Lung Carcinoma", *Biochem Int*, (1989), 19(3):489–496. (Abstract).

de Smidt, P.C., et al., Characteristics Of Association Of Oleoyl Derivatives Of 5–Fluorodeoxy.

Uridine And Methotrexate With Low–Density Lipoproteins (Ldl), *Pharm Res*, (1992), 9(4):565–569.

Deutsch, H.F., et al., "Cytotoxic Effects Of Daunomycin–Fatty Acid Complexes On Rat Hepatoma", Cells, *Cancer Res*, (1983), 43:2668–2672.

D'Orlando, et al., "Citicoline (CDP–Choline): Mechanisms of Action and Effects in Ischemic Brain Injury", *Neurol. Res.* (1995) 17:281–284.

Ehringer, W., et al., "A Comparison Of The Effects Of Linolenic (18:3 Omega 3) And Docosahexaenoic (22:6 Omega 3) Acids On Phospholipid Bilayers", *Chem Phys Lipids*, (1990), 54:79–88.

Ertel, et al., "Type III ω–Agatoxins: A Family of Probes for Similar Binding Sites on L– and N–Type Calcium Channels", *Biochemistry*, 33:5098–5108 (1994).

Falconer, J.S., et al., "Effect Of Eicosapentaenoic Acid And Other Fatty Acids On The Growth In Vitro Of Human Pancreatic Cancer Cell Lines", *Br. J. Cancer*, (1994,) 69:826–832.

Ferrari et al., "9–Cis–6,6'–Diapo–Gamma, Gamma–Carotenedioic Acid Derivatives And Pharmaceutical Compositions Containing Them", p. 710. Abs. 20423w, *Chem. Abs.* 95(23), 12/7/81, EP30,009 06/10/81.

Georg et al., "The Medicinal Chemistry of Taxol", in "Taxol Science and Applications" ed. Matthew Suffness. Boca Raton: CRC Press, Inc., 1995, pp. 317–375.

Hesse et al., "Inhibitory Effect of Cholesteryl– γ–Aminobutyrate" Neurolpharmacology, vol. 24, No. 2, pp. 139–146 (1985).

Higuchi et al., (Editors), Prodrugs as Novel Drug Delivery Systems, Acs Symposium Series, vol. 14, ACS, Washington, 1975, pp. 14–15.

Iwakami, et al., "Inhibition of Arochidonate 5–Lipoxygenase by Phenolic Compounds", Chem. Pharm. Bull. (Japan), 34(9), 3960–3963 (1986).

Jacob, et al., γ–Aminobutyric Acid Esters.1. Synthesis . . . , Journal of Medicinal Chemistry, vol. 28, No. 1, pp 106–110 (1985).

Jacobson, K., et al., Adenosine analogs with covalently attached lipids have enhanced potency at A1–adenosine receptors, *FEBS Letters* 225:1,2:97–102, (1987).

Jenski, L.J., et al., "Docosahexaenoic Acid–Induced Alteration Of Thy–1 And Cd8 Expression On Murine Splenocytes", *Biochim Biophys Acta*, (1995), 1236(1):39–50.

Jenski, L.J., et al. "Omega 3 Fatty Acids Increase Spontaneous Release Of Cytosolic Components From Tumor Cells", *Lipids*, (1991), 26(5):353–358.

Jenski, L.J., et al., "Omega–3 Fatty Acid–Containing Liposomes In Cancer Therapy", *Proc. Soc Exp Biol Med*, (1995), 210(3):227–233.

Kinsella, J.E., et al., "Effects Of Polyunsaturated Fatty Acids On The Efficacy Of Antineoplastic Agents Toward L5178y Lymphoma Cells", *Biochem Pharmacol*, (1993), 45(9):1881–1887. (Abstract).

Kretsinger, R. H., et al., "The EF–Hand, Homologs and Analogs", *Novel Calcium–Binding Proteins*, 17–37 (1991).

Madhavi, N., et al., "Effect Of N–6 And N–3 Fatty Acids On The Survival Of Vincristine Sensitive And Resistant Human Cervical Carcinoma Cells In Vitro", *Cancer Lett*, (1994), 84:31–41.

Makino, et al., Chemical Abstracts, vol. 106, No. 12, (90177x) issued Mar. 23, 1987, "Pharmaceuticals Permeable to Blood–Brain Barrier".

Marsden, B. J., et al., "H NMR Studies of Synthetic Peptide Analogues of Calcium–Bining Site III of Rabbit Skeletal Troponin C: Effect of the Lanthanum Affinity of the Interchange of Aspartic Acid and Asparagine Residues at the Metal Ion Coordinating Positions", *Biochemistry*, 27:4198–4206 (1988).

Mazumdar, et al., "Preparation and Evaluation of Ethambutol Derivatives", Indian J. Pharm. Sci. 47(6): 179–180 (1985).

Nicolaou et al., "Design, Synthesis and Biological Activity of Protaxols", *Nature*, 364: 464–466 (Jul.).

Nishio, et al., "Novel Water–soluble Derivatives of Docosahexaenoic Acid Increase Diacyl–Glycerol Production Mediated by Phosphatidylcholine–Specific Phospholipase C", *Proc. Soc. Exp. Biol. Med.* (1993) 203(2):200–208.

Oshima, M., et al., "Effects Of Docosahexaenoic Acid (Dha) On Intestinal Polyp Development In Apc Delta 716 Apc Delta 716 Knockout Mice", *Carcinogenesis*, (1995), 16(11):2605–2607.

Pascale, A.W., et al., "Omega–3 fatty acid modification of membrane structure and function. Alteration by docosahexaenoic acid of tumor cell sensitivity to immune cytolysis", *Nutr Cancer*, (1993), 19(2):147–157.

Plumb, J.A., et al., "Effect Of Polyunsaturated Fatty Acids On The Drug Sensitivity Of Human Tumour Cell Lines Resistant To Either Cisplatin Or Doxorubicin", *Br J Cancer*, (1993), 67:728–733.

Rocco et al., "Models of Fibronectin", The EMBO Journal, 6: 2343–2349 (1987).

Rose, W.C., Preclinical Antitumor Activity of Taxanes, in "Taxol Science and Applications" ed. Matthew Suffness. Boca Raton: CRC Press, Inc., 1995, pp. 317–375.

Schabitz, et al., "The effects of Prolonged Treatment with Citicoline in Temporary Experimental Focal Ischemia", *J. Neurol. Sci.*, (1996) 138(1–2):21–25 (Abstract).

Shashoua, et al., γ–Aminobutyric Acid Esters.1. Synthesis . . . , *J. of Med. Chem.*, vol. 27, pp. 659–664 (1984).

Shea, et al., *Developmental Brain Research*, 21:307–314 (1985).

Spector, R., "Fatty Acid Transport Through the Blood–Brain Barrier.", *J. of Neurochem.*, 50:2:639–643 (1988).

Suphioglu, C., et al., "Molecular Cloning and Immunological Characterization of Cyn d 7, A Novel Calcium–Binding Allergin from Bermuda Grass Pollen", *FEBS Letters*, 402:167–172 (1997).

Swindell, et al., "Characterization of the Taxol Structure–Activity Profile for the Locus of the A–Ring Side Chain Side Chain", *Bioorganic & Medicinal Chem. Ltrs.*, vol. 4, No. 12, pp. 1531–1536. (1994).

Tessier, C., et al., "Docosahexaenoic Acid Is A Potent Inhibitor Of Rat Uterine Stromal Cell Proliferation", *Biochem Biophys Res Commun*, (1995), 207(3): 1015–1021.

Tinsley, I.J., et al., "Influence Of Dietary Fatty Acids On The Incidence Of Mammary Tumors In The C3h Mouse", Ch3h Mouse, *Cancer Res*, (1981), 41:1460–1465.

Young, et al., *FEBS Letters*, 338:212–216 (1994).

Zerouga, M., et al., "Phospholipid Class As A Determinant In Docosahexaenoic Acid's Effect On Tumor Cell Viability", *Anticancer Res*, (1996), 16:2863–2868. (Abstract).

Zijlstra, J.G., et al., "Influence Of Docosahexaenoic Acid In Vitro On Intracellular Adriamycin Concentration In Lymphocytes And Human Adriamycin–Sensitive And Resistant Small–Cell Lung Cancer Cell Lines, And On Cytotoxicity In The Tumor Cell Lines", *Int J Cancer*, (1987), 40:850–856.

International Search Report, PCT/US 00/06160, International Filing Date: Sep. 3, 2000.

* cited by examiner

DHA-PHARMACEUTICAL AGENT CONJUGATES TO IMPROVE TISSUE SELECTIVITY

This application is a continuation of prior application Ser. No. 09/135,291, filed on Aug. 17, 1998 entitled "DHA-Pharmaceutical Agent Conjugates Of Taxanes" and now abandoned, which is a continuation of Ser. No. 08/651,312 filed May 22, 1996, now U.S. Pat. No. 5,795,909.

BACKGROUND OF THE INVENTION

Improving drug selectivity for target tissue is an established goal in the medical arts. In general, it is desirable to deliver a drug selectively to its target, so that dosage and, consequently, side effects can be reduced. This is particularly the case for toxic agents such as anti-cancer agents because achieving therapeutic doses effective for treating the cancer is often limited by the toxic side effects of the anti-cancer agent on normal, healthy tissue. The problems relating to lack of drug selectivity can be exemplified by Taxol®.

Taxol® (paclitaxel) was first isolated in 1971 from the bark of Taxus brevifolia and was approved in 1992 by the US Food and Drug Administration for treatment of metastatic ovarian cancer and later for breast cancer. Its mechanism of action is believed to involve promoting formation and hyperstabilization of microtubules, thereby preventing the disassembly of microtubules necessary for completion of cell division. It also has been reported that Taxol induces expression of cytokines, affects the activity of kinases and blocks processes essential for metastasis, in as yet uncharacterized mechanisms of action.

Taxol has attracted unusually strong scientific attention, not only because of its unique antiproliferative mechanism of action, but also because it is active against nearly all cancers against which it has been tested and because it has been discovered to be an analog of numerous closely related compounds occurring naturally. These compounds, taxanes, are now recognized as a new class of anticancer compounds.

Taxol's strength against cancers of diverse tissue origin also represents a significant drawback. An ideal anticancer agent has tissue specificity, thereby reducing side-effects on normal (dividing) cells. Taxol analogs with tissue specificity therefore are desired. Another drawback of Taxol is its extreme insolubility. Taxol can be administered effectively in a solvent including cremophor, which combination can provoke severe hypersensitive immune responses. As a result of these drawbacks, and also as a result of the potential for modifying Taxol at numerous sites as demonstrated by other naturally-occurring taxanes with anticancer activity, a search for more selective taxanes was launched.

To date, more than 200 taxanes have been synthesized (or isolated) and tested in vitro or in vivo for anticancer activity. The results, however, have been so disappointing that the National Cancer Institute (NCI) generally no longer is interested in testing Taxol analogs. In general with Taxol analogs, the solubility problems remain, and/or potency is sharply reduced, and/or selectivity is not improved, and/or the ratio of the median toxic dose to the median effective dose ("therapeutic index") is unacceptably reduced.

Taxol has the following formula:

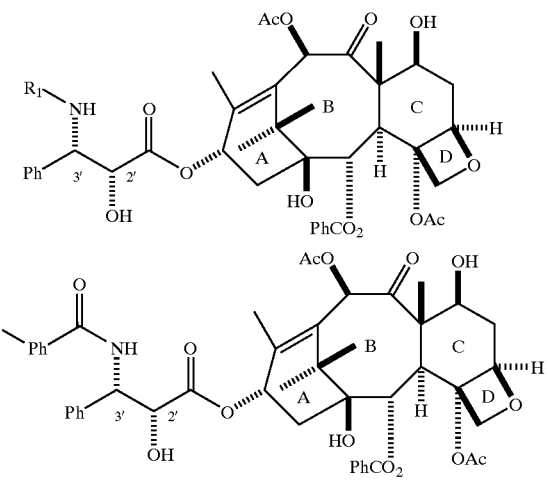

Taxanes have the basic three ring structure (A. B and C), substituted or unsubstituted.

Taxol's carbons are numbered conventionally as follows:

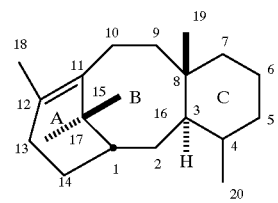

Based upon the taxanes tested to date, as many questions have been raised as have been answered, and general rules have not been fashioned easily in predicting selectivity, activity and solubility. Firstly, no rules have emerged regarding selectivity. Those taxanes that are strongly active appear to have activity as broad as Taxol's activity, and no headway appears to have been made in terms of developing a more selective Taxol analog.

Some information about activity has emerged. Numerous substitutions have been made at C7, C9, C10, C19, $R_1$ and combinations thereof while retaining significant, but usually reduced, activity. Substitutions at C2, C4 and 2'OH, however, are generally not tolerated. These conclusions are only generalities, for example, because some substitutions at C9–C10 (cyclic derivatives) are not tolerated and some substitutions at C2 (meta substitutions on the phenyl) are tolerated. Likewise, the C13 side chain and, in particular, the 2'OH are required, although the minimum structural requirements of the side chain have not been determined for therapeutic efficacy.

Attempts to improve Taxol's solubility have not resulted in successful clinical products. One approach has been to manufacture prodrugs of Taxol, which prodrugs undergo in vivo transformation into Taxol and some other product. Attempts were made to esterify the C7 hydroxy and 2' hydroxy groups, with the hope that the bond would be stable in solution (to permit preferred administration modes—i.v. over at least 24 hours) but would cleave readily in vivo. The groups tested were all hydrophilic and included amines, short carboxylic acids (using e.g. succinic anhydride and glutaric anhydride), sulfonic acids, amino acids and phosphates. Generally, activity was reduced although some success was obtained with certain derivatives. Again, no particular pattern emerged permitting one to predict reliably which groups could be substituted on Taxol to yield a therapeutically useful product, although it was suggested that the 2' OH derivatives may cleave more easily than the C7 OH derivatives.

Several other factors add to the problem of predicting which Taxol analogs will be effective. Multiple mechanisms of action have been proposed in the literature, and a change in one position may have no effect on activity on one such mechanism but may eliminate activity on another mechanism. In addition, changes that favorably influence activity may unfavorably influence bioavailability. For example, Taxol affects microtubule formation inside a cell, but a change in structure that increases intracellular activity may adversely affect the ability of Taxol to gain entry into a cell. Taxol also is known to bind to proteins, and the effect on activity that results from a change in Taxol's binding to protein (in terms of conformation, cellular absorption and solubility) is unknown.

It has been reported that Taxol does not get into the brain, apparently excluded by the blood brain barrier. It is not known why this is so, as Taxol is lipophilic, gets into cells and might be expected to cross the blood brain barrier.

Among the most promising of the two hundred analogs tested is Taxotere (docetaxel), because of its slightly increased activity and solubility. Oddly, however, Taxotere differs from Taxol at sites which typically do not have a strong influence on activity, and one would not predict the improvements in Taxotere from these differences, even in hindsight.

Taxotere has the following formula:

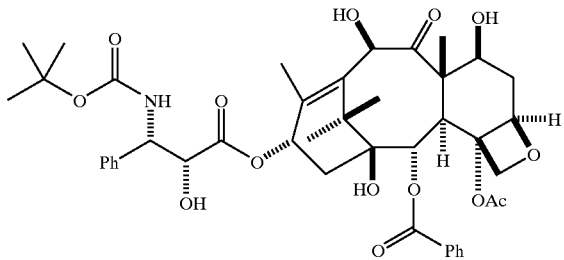

DHA (docosahexaenoic acid) is a 22 carbon naturally-occurring, unbranched fatty acid that previously has been attached to drugs to help deliver them across the blood brain barrier. DHA is attached via the acid group to hydrophilic drugs and renders these drugs more hydrophobic (lipophilic). DHA is an important constituent of the brain and recently has been approved in Europe as an additive to infant formula. It is present in the milk of lactating women. The mechanism of action by which DHA helps drugs conjugated to it cross the blood brain barrier is unknown.

SUMMARY OF THE INVENTION

The present invention involves the unexpected finding that conjugates of pharmaceutical agents and a highly lipaphilic group, a C22 unbranched carbon chain, have a different selectivity relative to the unconjugated pharmaceutical agents. The conjugates, in general, render the activity of these compounds selective for colon tissue, breast tissue and central nervous system tissue ("targeted tissues"). The conjugates, also unexpectedly, restrict the activity of these compounds to cell types within these tissue categories relative to that of the unconjugated pharmaceutical agents. The conjugates, further unexpectedly, reduce sharply the activity of these compounds relative to that of the unconjugated pharmaceutical agents in most cell lines of tissue types other than colon, breast, and central nervous system, thereby reducing potential side effects of the conjugates versus those of the unconjugated pharmaceutical agents. The therapeutic index of the conjugates may be improved, versus that of the unconjugated pharmaceutical agents.

According to one aspect of the invention, a method is provided for targeting a pharmaceutical agent to a noncentral nervous system tissue to treat a noncentral nervous system condition. A covalent conjugate of cis-docosahexanoic acid and a pharmaceutical agent effective for treating said condition is administered to a subject in need of such treatment. In preferred embodiments, the tissue is breast tissue, gastrointestinal tissue and ovarian tissue and the condition calls for treatment of breast tissue, gastrointestinal tissue or ovarian tissue, respectively.

The pharmaceutical agent may be any pharmacological compound or diagnostic agent, as desired. The pharmaceutical agent, of course, has an activity outside of the central nervous system.

Examples of catagories of pharmaceutical agents include: adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; antiarthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; antiemetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobsessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; antiurolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator, immunostimulant; immunosuppressant; impotence therapy adjunct; inhibitor; keratolytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine Al antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; treatment of amyotrophic lateral sclerosis; treatment of cerebral ischemia; treatment of Paget's disease; treatment of unstable angina; uricosuric; vasoconstrictor; vasodilator; vulnerary; wound healing agent; xanthine oxidase inhibitor.

In one particularly preferred embodiment of the invention, the pharmaceutical agent is an anti-cancer agent. Examples of anti-cancer agents are described in greater detail in the specification. Included specifically are the taxanes (e.g., Taxol and Taxotere). Conjugates of cis-docosahexanoic acid and taxoids also are embraced by the invention.

Cis-docosahexanoic acid previously has been conjugated to drugs that are active in the central nervous system. The present invention contemplates the use of cis-docosahexanoic acid in the manufacture of a medicament for treating a noncentral nervous system condition. The invention further contemplates compositions of matter that are covalent conjugates of cis-docosahexanoic acid and noncentral nervous system active pharmaceutical agents. A non-central nervous system active pharmaceutical agent is one that has no function or use in the central nervous system. Its only therapeutic use is outside of the central nervous system. Examples of such agents include, but are not limited to: Blood glucose regulators, such as tolazamide, tolbutamide, chlorpropamide, acetohexamide, and, glipizide; HMGcoA reductase inhibitors, such as Lovastatin (Mevacor), Simvastatin (Zocor), Pravastatin (Pravachol), and, Fluvstatin (Lescol); Muscosal Protectives, such as Misoprostol (Cytotec); Gastrointestinal motility affectors, such as Cisapride (Propulsid), Metoclopramide (Reglan), and, Hyoscyamine (Levsin); Antidiarrheals, such as Diphenoxylate hydrochloride (Lomotil), Metronidazole (Flagyl), Methylprednisolone (Medrol), and, Sulfasalazine (Azulfidine); and Hormones for treating, inter alia, ovarian conditions, such as Progesterone, Norgestrel, Norethynodrel, Norethindrone, Levonorgestrel, Ethyndiol, Mestranol, Estrone, Equilin, 17 alpha dihydroequilin, equilenin, 17 alpha dihydroequilenin, 17 alpha esradiol, 27 bea estradiol, Leuprolide (Lupron), Testolactone, Climiphene, urofollitropin, bromocriptine, gonadorelin, danazol, dehydroepiandrosterone, androstenedione, dihydrotestosterone, Relaxin, folliculostatin, Follicle regulatory protein, Gonadocrinins, Oocyte maturation inhibitor, and, Insulin growth factor. Other compounds are detailed below.

The methods and/or products of the invention are useful for treating a variety of medical conditions including conditions involving abnormal mammalian-cell proliferation. They further are useful in treating diabetes and its complications, excess acid secretion, cardiovascular conditions involving cholesterol (e.g., hyperlipidemia and hypercholesterolemia), diarrhea, ovarian diseases (e.g. endometriosis, ovarian cysts, etc.) and as contraceptive agents. Other conditions treatable according to the invention will be apparent to those skilled in the art based upon the disclosure and lists of compounds provided.

The methods and/or products of the invention also are useful in treating conditions specific to noncentral nervous system tissue. Such conditions can be specific to breast tissue, gastrointestinal tissue and ovarian tissue. The tissue also may be other noncentral nervous system tissues. Noncentral nervous system tissue includes tissue of the: Blood and Blood Forming system: including platelets, blood vessel wall, and bone marrow; Cardiovascular system: including heart and vascular system; Digestive and excretory system: including alimentary tract, biliary tract, kidney, liver, pancreas and urinary tract; Endocrine system: including adrenal gland, kidney, ovary, pituitary gland, renal gland, salivary gland, sebaceous gland, testis, thymus gland and thyroid gland; Musclar system: including muscles that move the body. Reproductive System: including breast, ovary, penis and uterus; Respiratory system: including bronchus, lung and trachea; Skeletal system: including bones and joints; Tissue, fiber, and integumentary system: including adipose tissue, cartilage, connective tissue, cuticle, dermis, epidermis, epithelium, fascia, hair follicle, ligament, bone marrow, melanin, melanocyte, mucous membrane, skin, soft tissue, synovial capsule and tendon.

Figure 1:
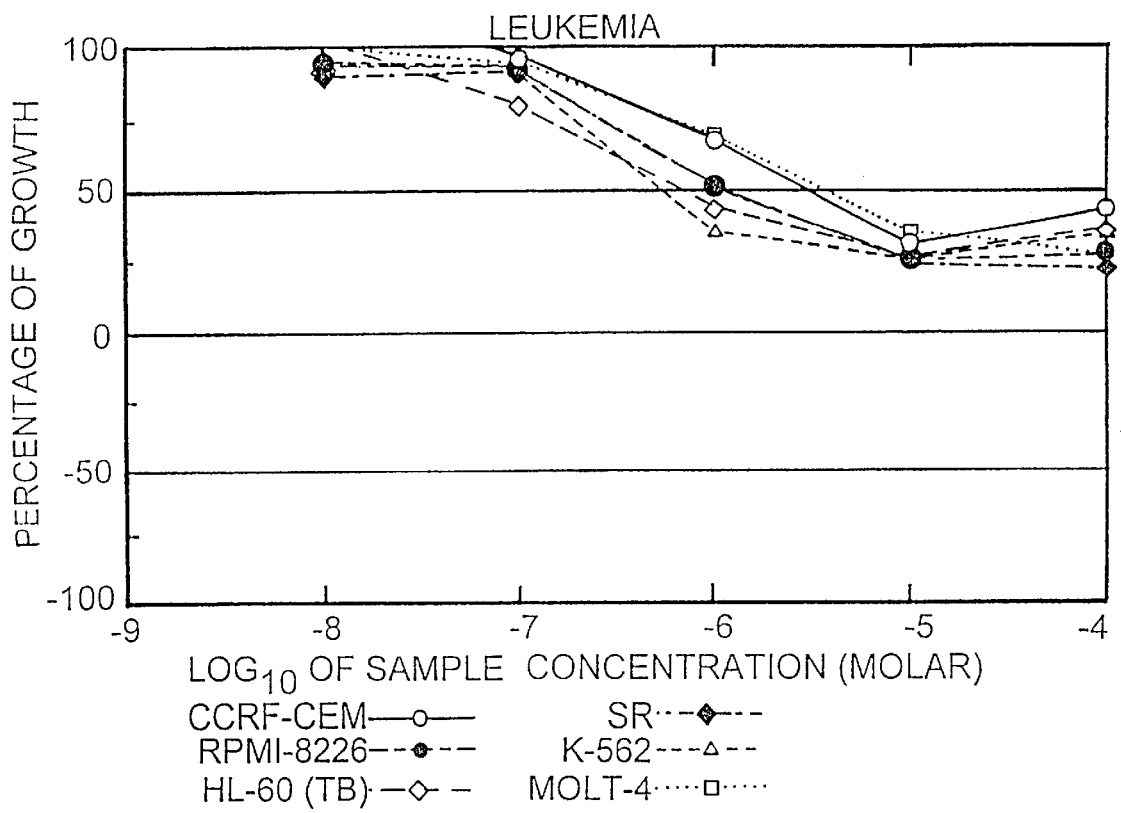
FIG. 1 is a graph plotting concentration of conjugate 1 versus percent growth of leukemia cells.

DETAILED DESCRIPTION OF THE INVENTION cis-docosahexaenoic acid (DHA) is a naturally occurring fatty acid. It is an unbranched chain fatty acid with six double bonds, all cis. Its structure is as follows:

DHA can be isolated, for example, from fish oil or can be chemically synthesized. These methods, however, can generate trans isomers, which are difficult and expensive to separate and which may present safety problems in humans. The preferred method of production is biological synthesis to produce the all cis isomer. The preferred source of DHA is from Martek Biosciences Corporation of Columbia, Md. Martek has a patented system for manufacturing DHA using microalgae which synthesize only a single isomer of DHA, the all cis isomer. Martek's patents include U.S. Pat. Nos. 5,374,657, 5,492,938, 5,407,957 and 5,397,591.

DHA also is present in the milk of lactating women, and Martek's licensee has obtained approval in Europe of DHA as a nutritional supplement for infant formula.

It is known that DHA can be unstable in the presence of oxygen. To stablizie DHA and its conjugates it is important to add anti-oxidants to the material after it is synthesized. One method of stablization is to make-up the newly synthesized material in the following solution: 100 g neat DHA-taxol plus 100 g of vehicle (100 ml propylene glycol, 70 mg alph-tocopherol, 5 mg dialaurylthiodipropionic acid, 50 mg ascorbic acid) prepared and held under argon in amber, sealed vials and stored at four degrees centigrade. The following anti-oxidants may also be employed: ascorbic acid, ascorbyl palmitate, dilauryl ascorbate, hydroquinone, butyated hydroxyanisole, sodium meta bisulfite, t-B carotene and x-tocopherol. A heavy metal chelator such as ethylenediamine tetra-acetic acid (EDTA) may also be used.

Paclitaxel was first isolated from the bark of Taxus brevifolia (Wani et al., *J. Am. Chem. Soc.,* 93, 2325, 1971). Its isolation and synthesis have been reported extensively in the literature. Applicants obtained paclitaxel from a commercial source, Hauser Laboratories, of Boulder, Colo.

EXAMPLE 1

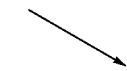

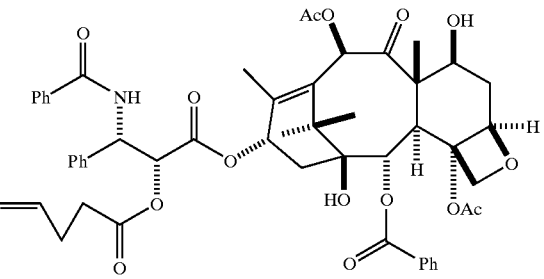

conjugate 1

A solution of Taxol (41 μmol) in methylene chloride (2.5 mL) under argon was mixed with 4-dimethylaminopyridine (41 μmol), dicyclohexylcarbodiimide (82/ μmol), and DHA (41 μmol) and the reaction mixture was stirred at ambient temperature for two hours. Following dilution with ether, the reaction mixture was washed with 5% hydrochloric acid, water, saturated aqueous sodium chloride, dried, and concentrated. Radial chromatography of the residue produced 45 mg (94%) of crystalline Taxol-DHA conjugate 1.

EXAMPLE 2

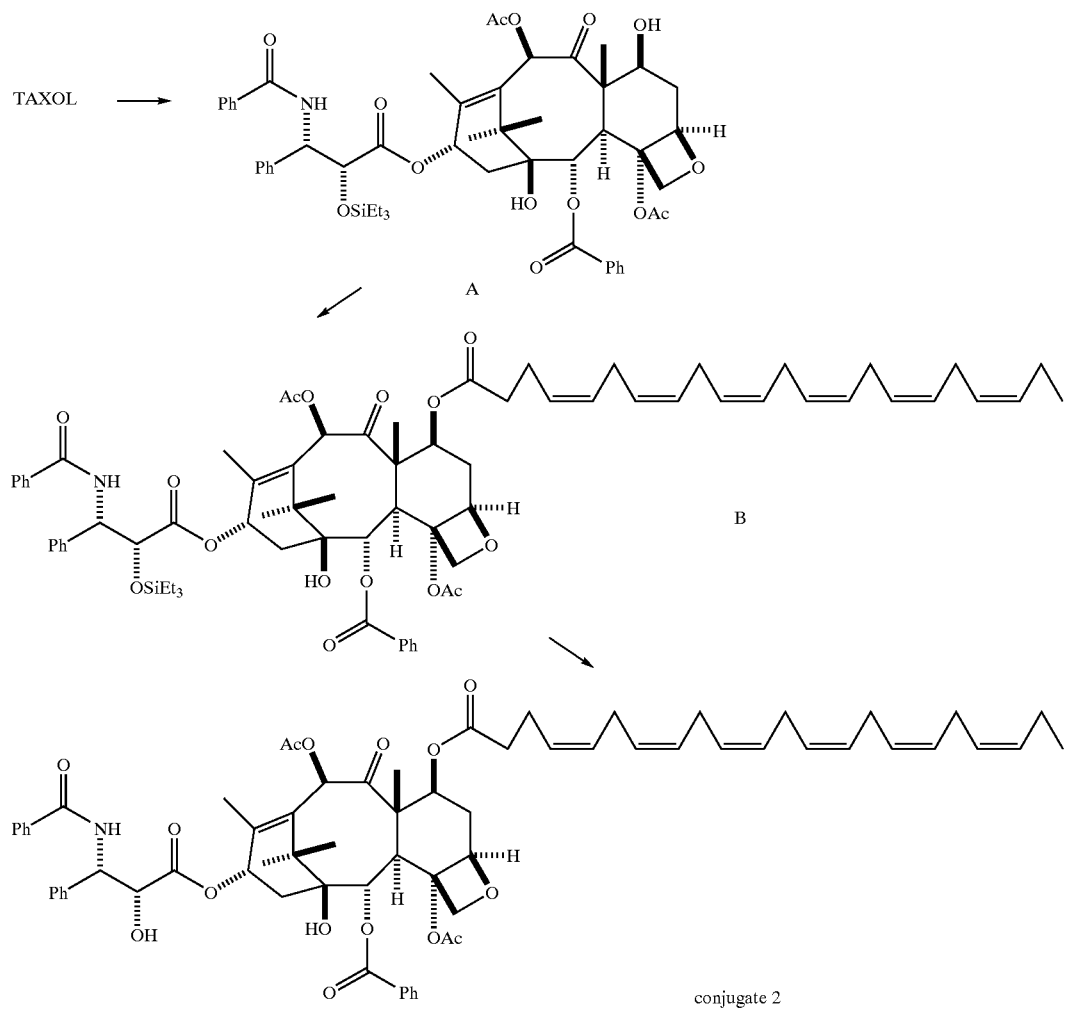

The production of analog 2 involves several steps including a number of protection-acylation-deprotection steps. A solution of Taxol (59 μmol) in methylene chloride (2.5 mL) was mixed at ambient temperature under argon with imidazole (147 μmol) and triethylsilyl chloride (147 μmol). The reaction mixture was stirred for thirty minutes, diluted with additional methylene chloride, washed with water, saturated aqueous sodium chloride, dried, and concentrated. Chromatography of the residue produced 50 mg (88%) of intermediate A plus 5 mg of the 2', 7-di(triethylsilyl) ether derivative. A solution of intermediate A (52 μmol) in methylene chloride (3 mL) was mixed at ambient temperature under argon with 4-dimethylaminopyridine (52 μmol), dicyclohexylcarbodiimide (104 μmol), and DHA (52 μmol). The reaction mixture was stirred for ten hours, diluted with ether, passed through celite, and concentrated. Chromatography of the residue produced 65.9 mg of intermediate B. A solution of intermediate B (51 μmol) in acetonitrile (2 mL) at 0° C. under argon was mixed with 49% aqueous HF (0.2 mL) and the reaction mixture was stirred for one hour. After dilution with ether, the reaction mixture was washed with water, saturated aqueous sodium chloride, dried, and concentrated. Radial chromatography of the residue produced 44.6 mg (75%) of Taxol-DHA conjugate 2.

EXAMPLE 3

Conjugates 1 and 2 were sent to the United States National Cancer Institute (NCI) for screening in the NCI's anticancer screening program. The conjugates were provided in ethanol (approximately 40 mg analog/2 ml ethanol). The conjugates were sealed in vials under argon to avoid exposure of the conjugates to oxygen because the conjugates were believed to be sensitive to oxygen. Instructions were provided to store at 4° C. and to open the vials only when ready for immediate experimental use. Instructions also were provided to use the ethanol solutions containing the conjugates directly or to dissolve the analogs further in DMSO (dimethylsulfoxide) at appropriate concentrations, with vortexing if necessary for adequate dispersal.

Figure 2:
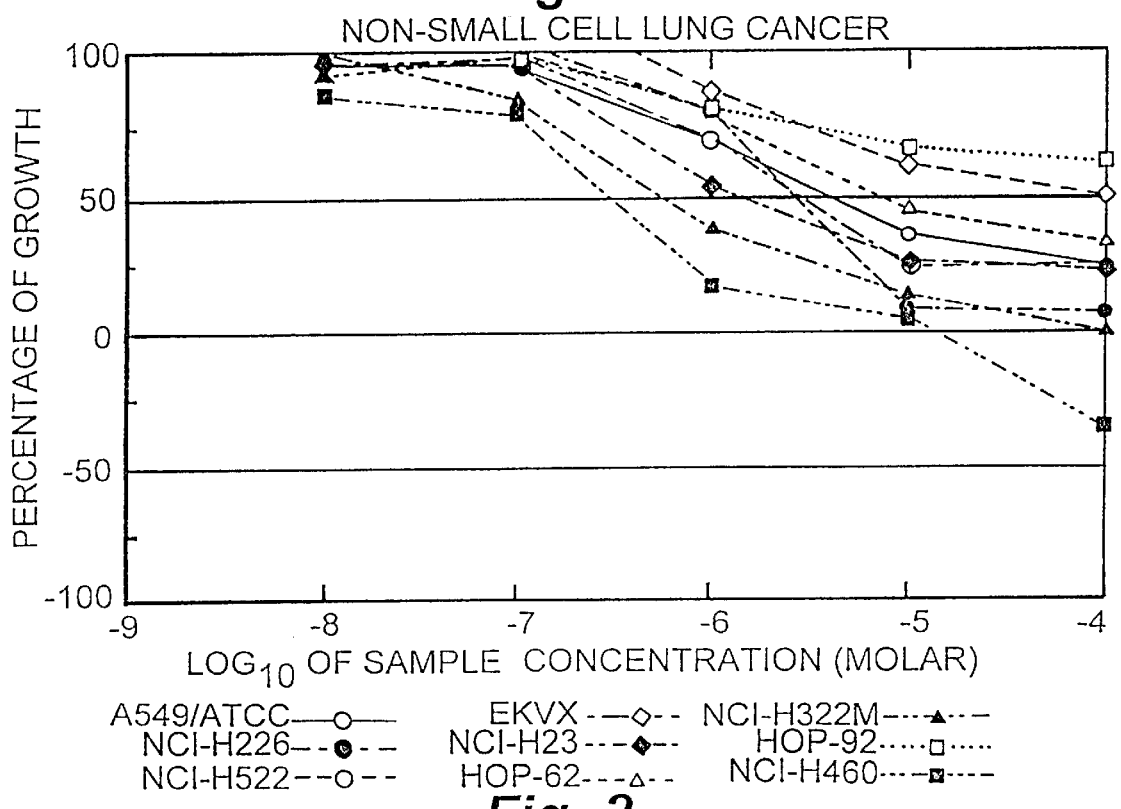
FIG. 2 is a graph plotting concentration of conjugate 1 versus percent growth of non-small cell lung cancer cells.
Figure 3:
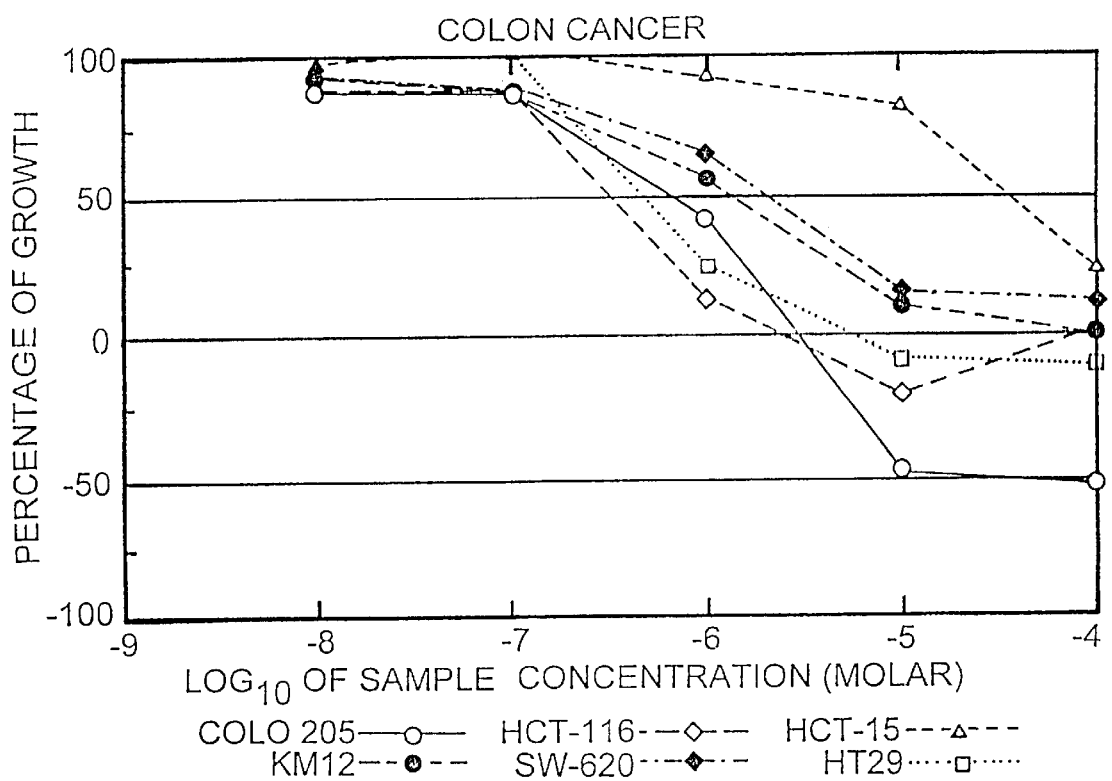
FIG. 3 is a graph plotting concentration of conjugate 1 versus percent growth of colon cancer cells.
Figure 4:
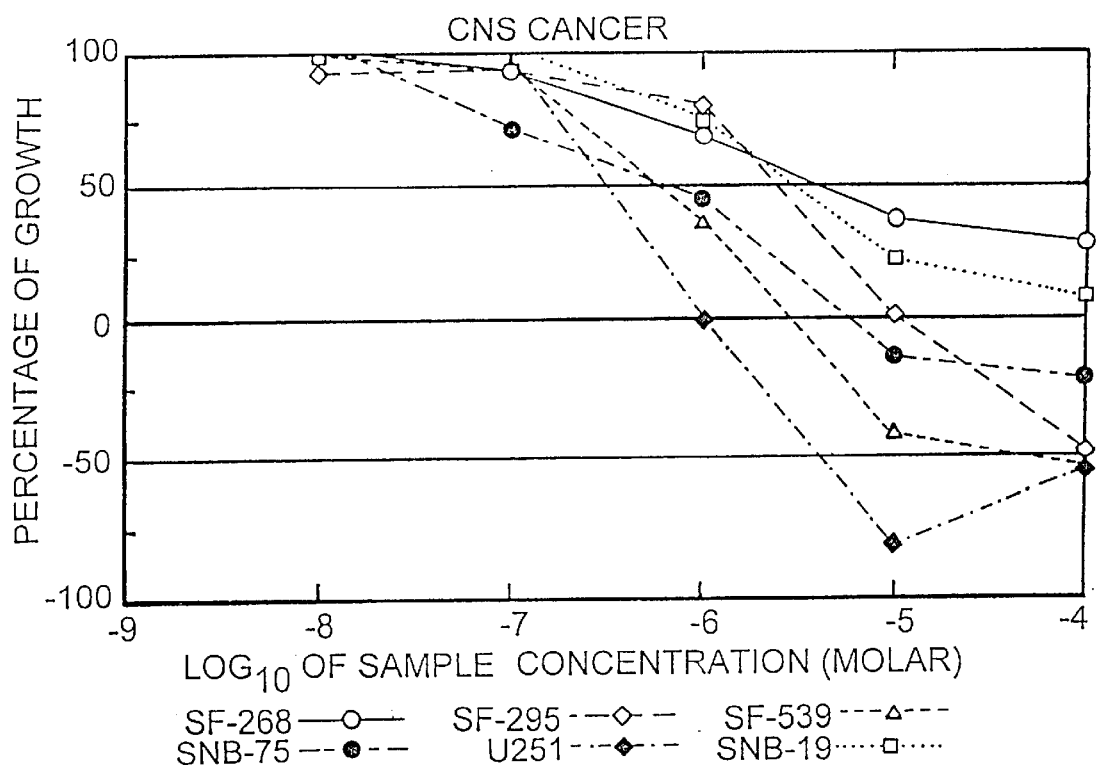
FIG. 4 is a graph plotting concentration of conjugate 1 versus percent growth of CNS cancer cells.
Figure 5:
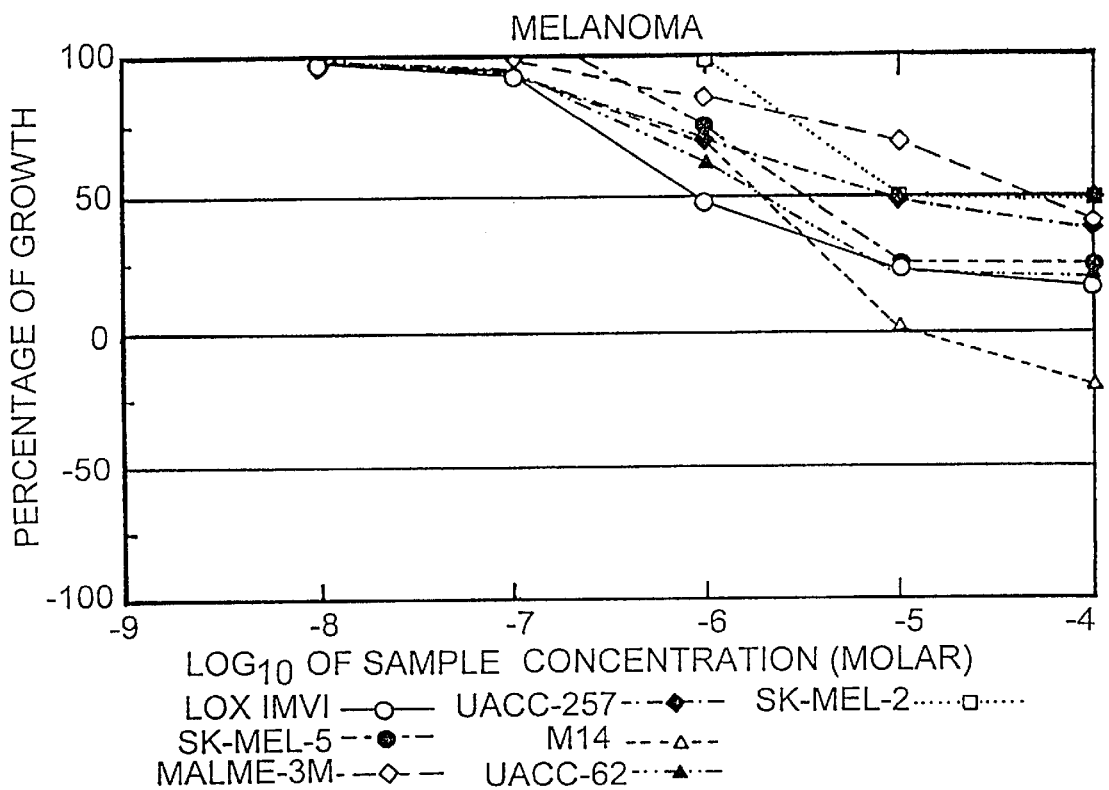
FIG. 5 is a graph plotting concentration of conjugate 1 versus percent growth of melanoma cells.
Figure 6:
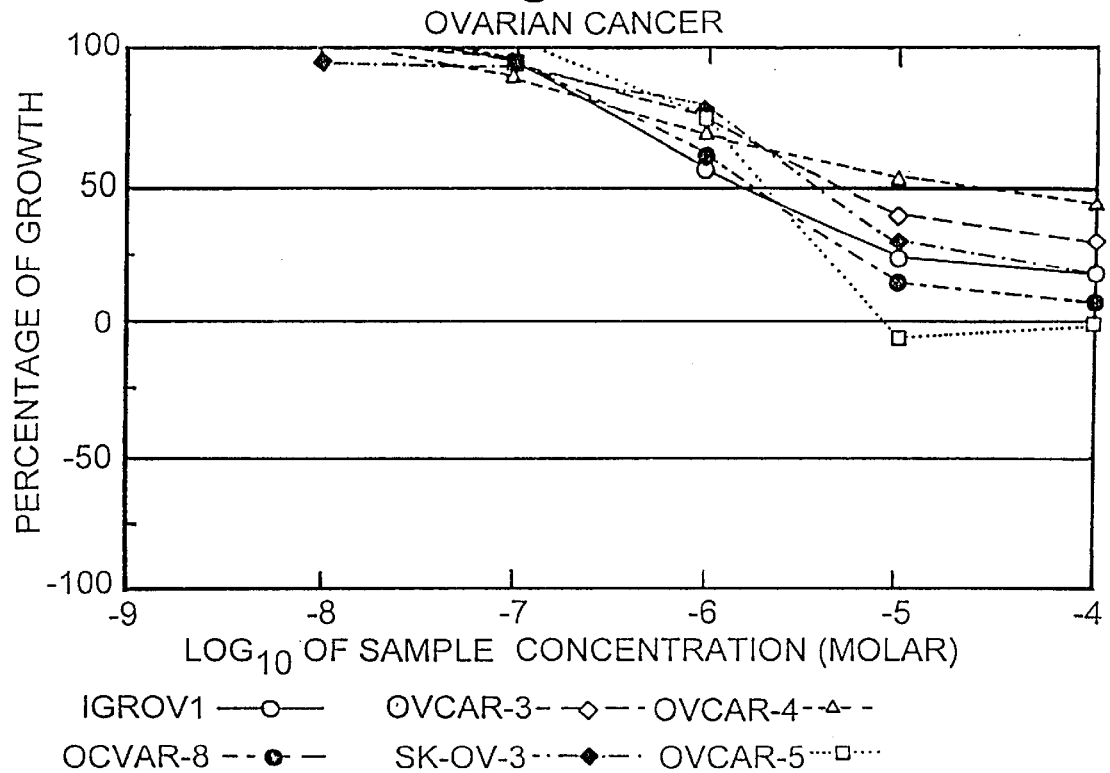
FIG. 6 is a graph plotting concentration of conjugate 1 versus percent growth of ovarian cancer cells.
Figure 7:
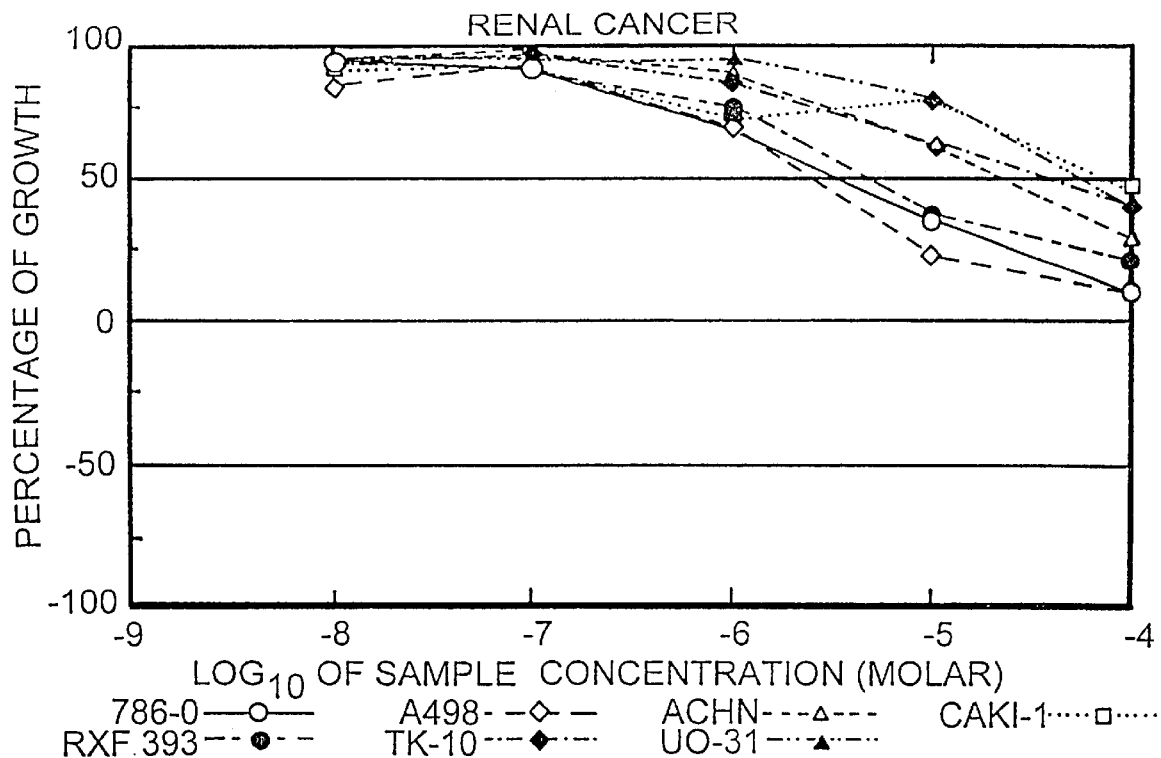
FIG. 7 is a graph plotting concentration of conjugate 1 versus percent growth of renal cancer cells.
Figure 8:
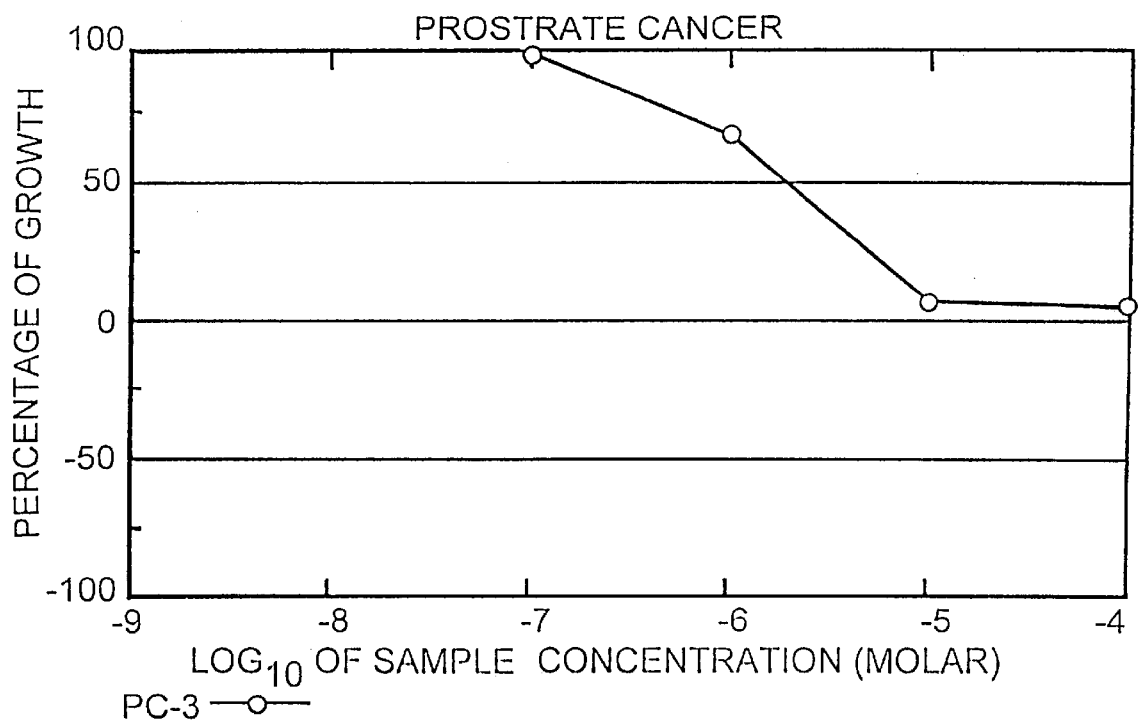
FIG. 8 is a graph plotting concentration of conjugate 1 versus percent growth of prostate cancer cells.
Figure 9:
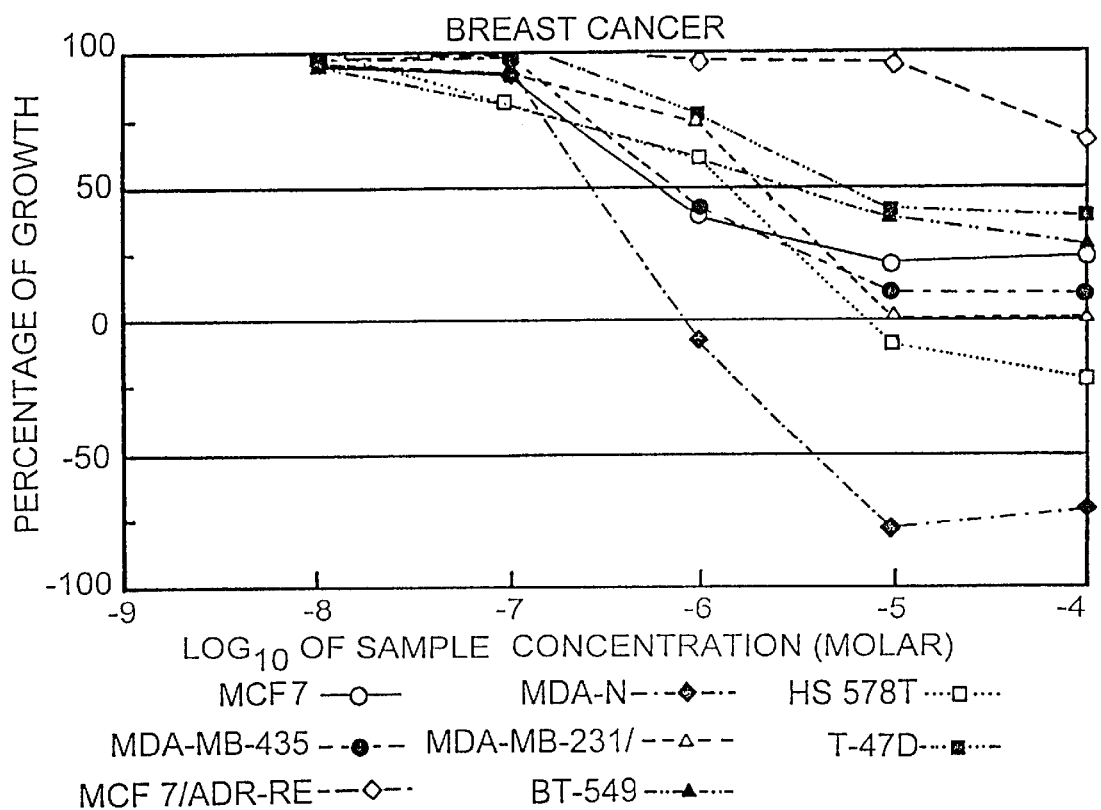
FIG. 9 is a graph plotting concentration of conjugate 1 versus percent growth of breast cancer cells.
Figure 10:
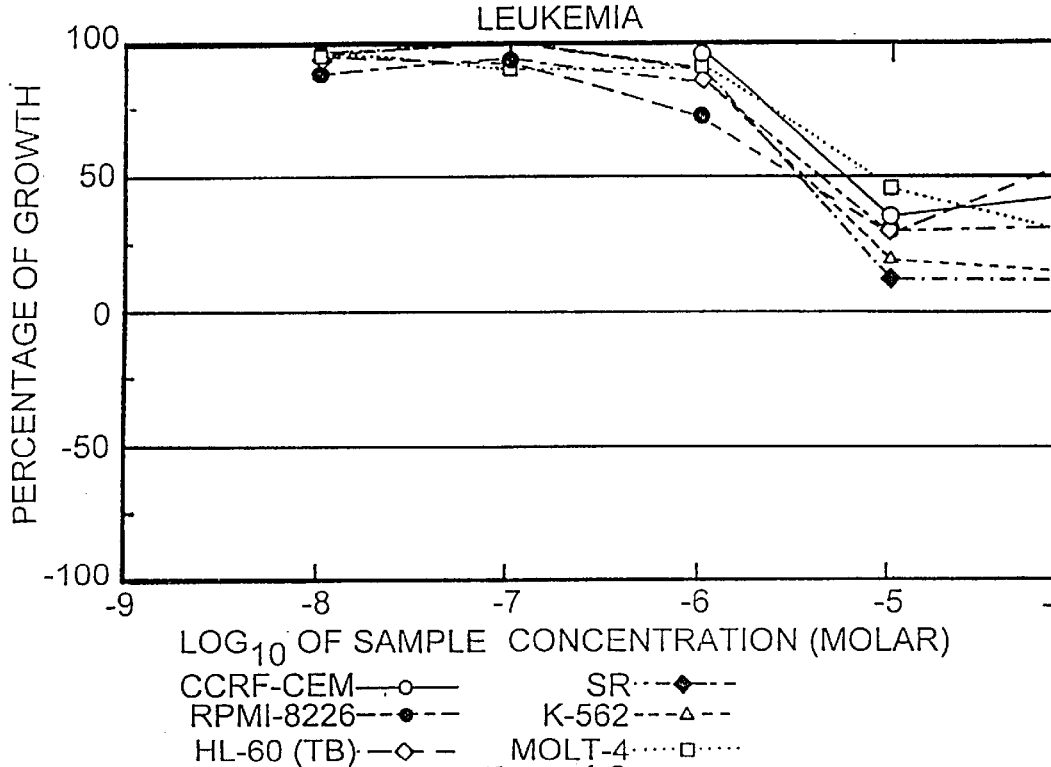
FIG. 10 is a graph plotting concentration of conjugate 2 versus percent growth of leukemia cells.
Figure 11:
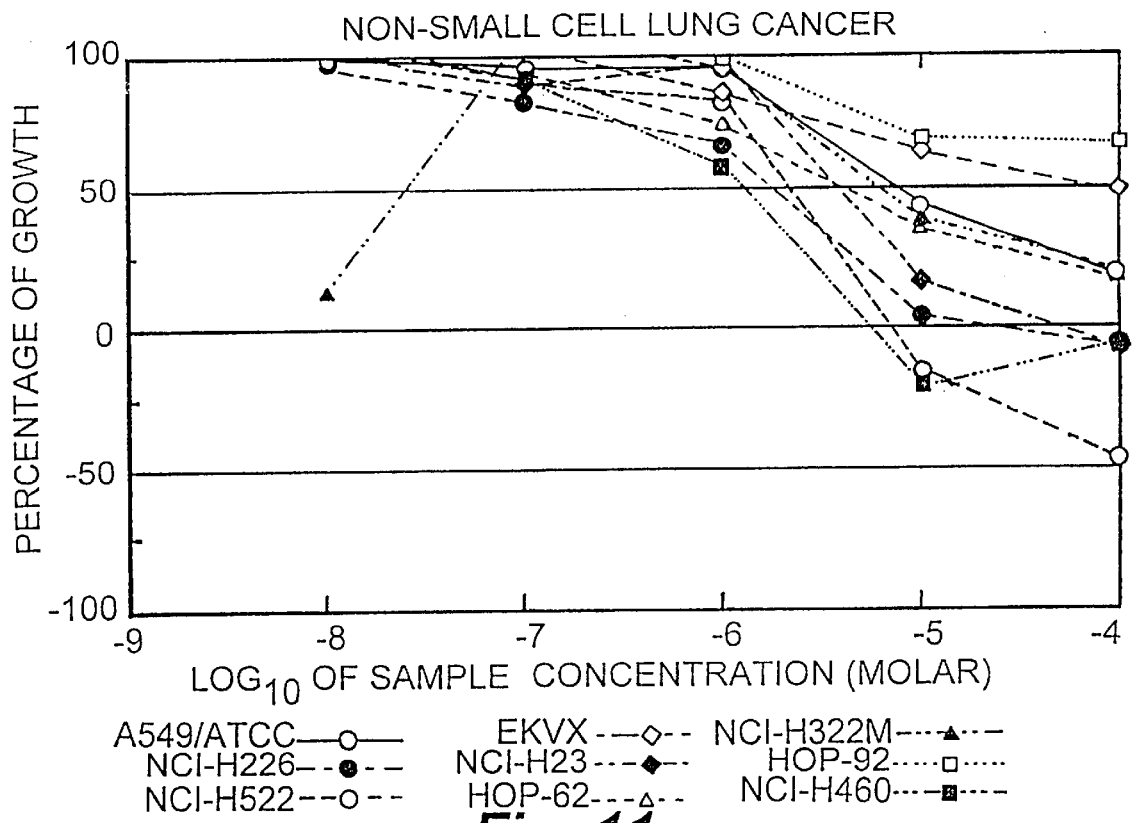
FIG. 11 is a graph plotting concentration of conjugate 2 versus percent growth of non-small cell lung cancer cells.
Figure 12:
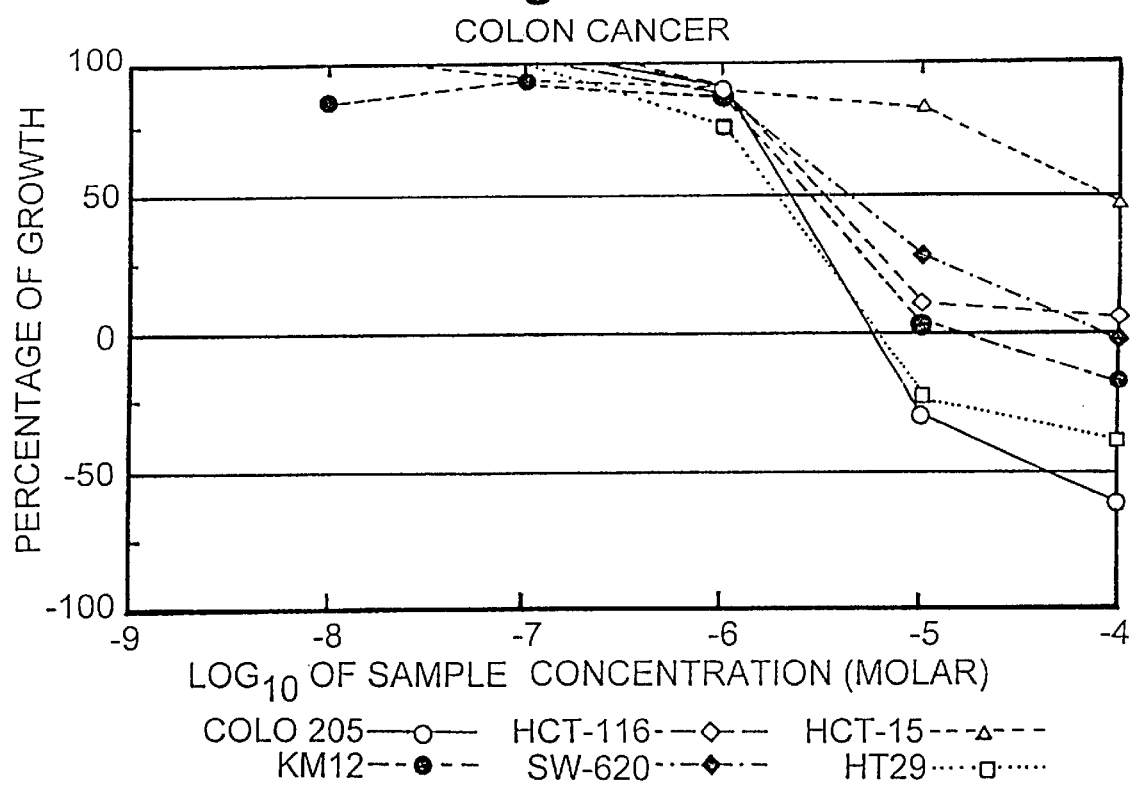
FIG. 12 is a graph plotting concentration of conjugate 2 versus percent growth of colon cancer cells.
Figure 13:
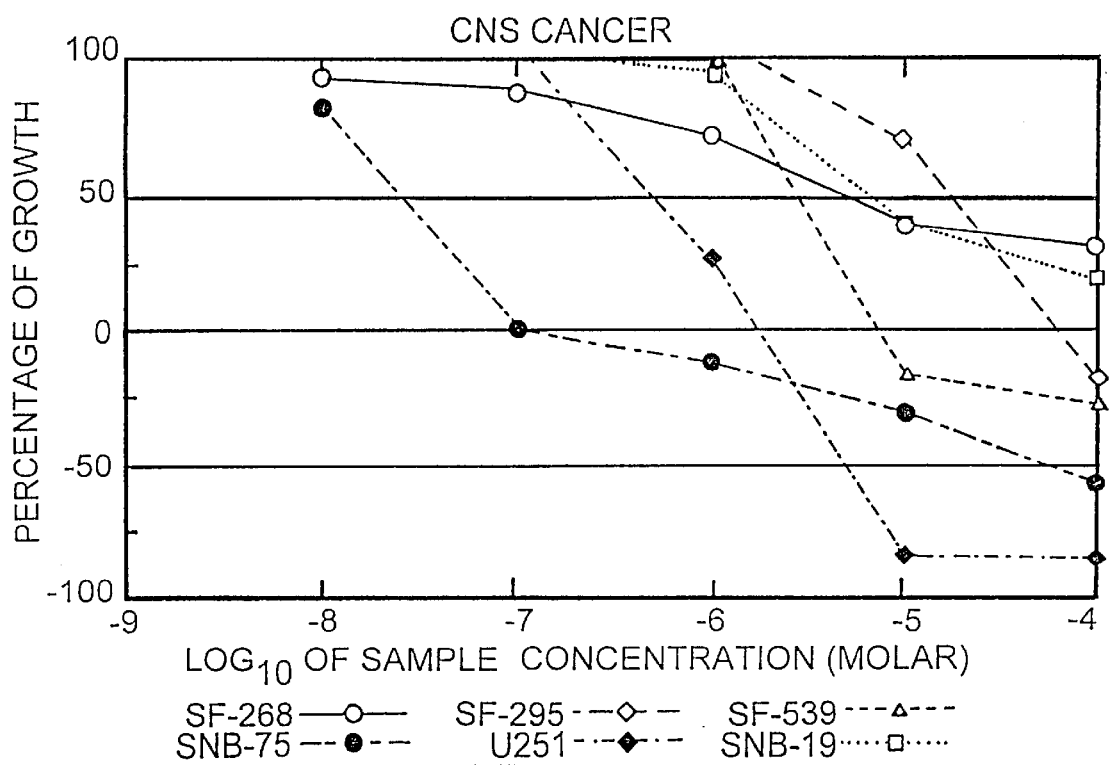
FIG. 13 is a graph plotting concentration of conjugate 2 versus percent growth of CNS cancer cells.
Figure 14:
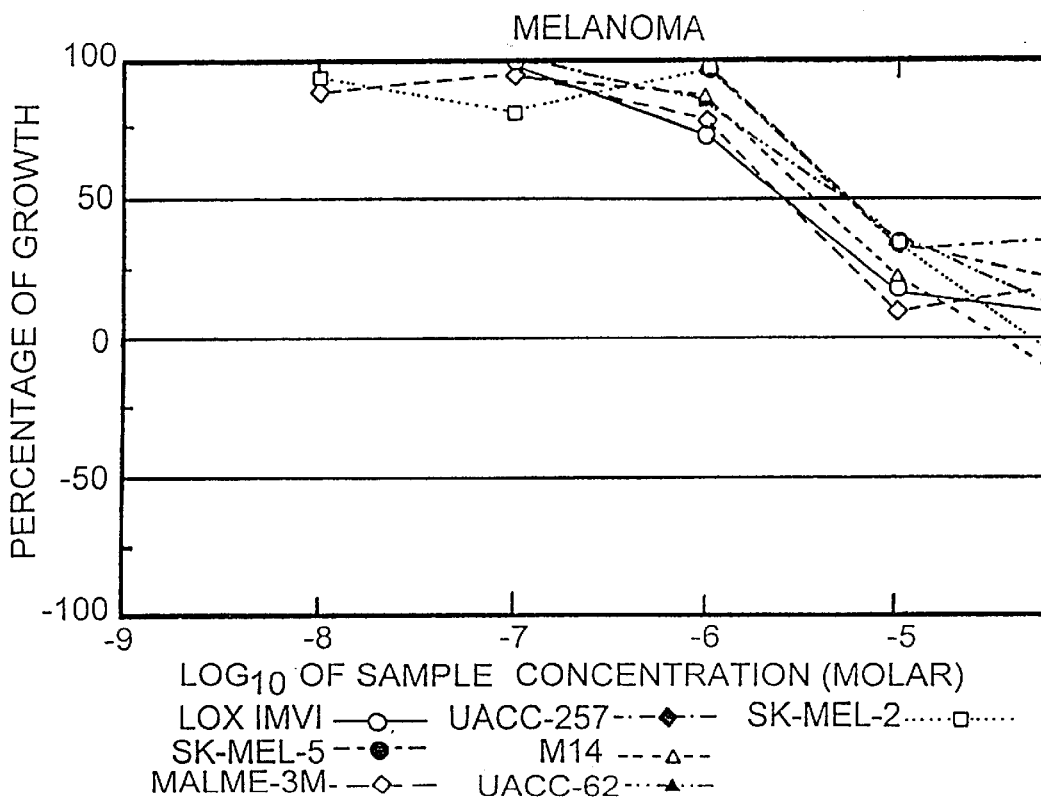
FIG. 14 is a graph plotting concentration of conjugate 2 versus percent growth of melanoma cells.
Figure 15:
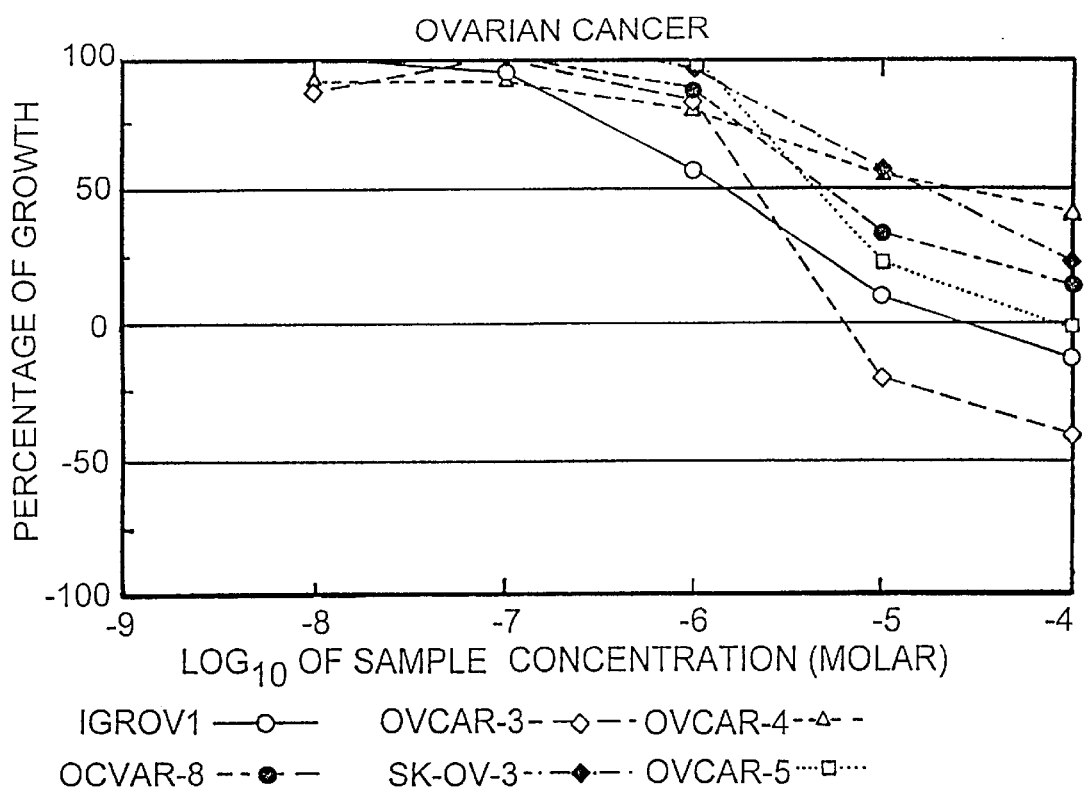
FIG. 15 is a graph plotting concentration of conjugate 2 versus percent growth of ovarian cancer cells.
Figure 16:
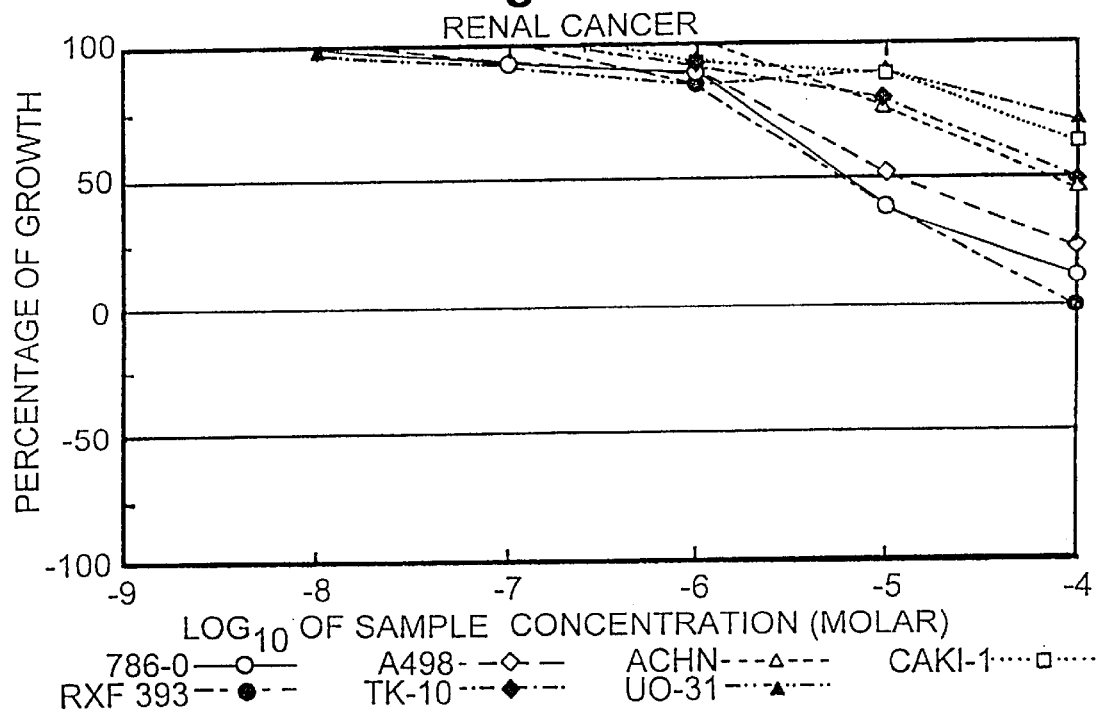
FIG. 16 is a graph plotting concentration of conjugate 2 versus percent growth of renal cancer cells.
Figure 17:
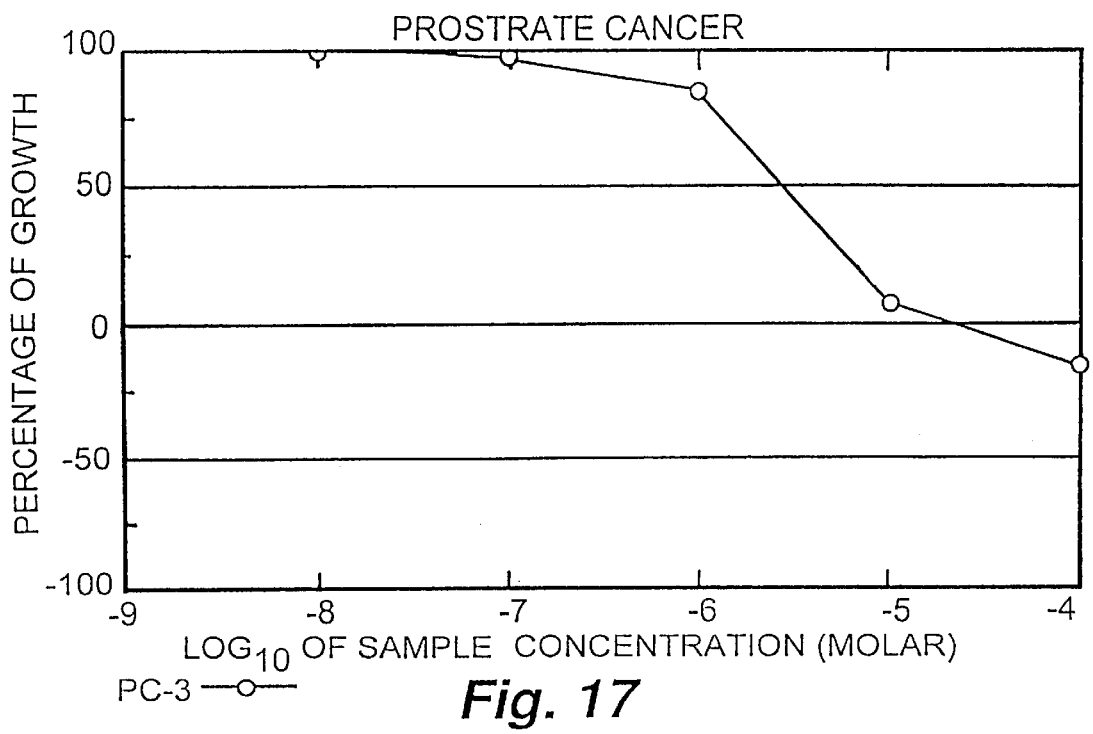
FIG. 17 is a graph plotting concentration of conjugate 2 versus percent growth of prostate cancer cells.
Figure 18:
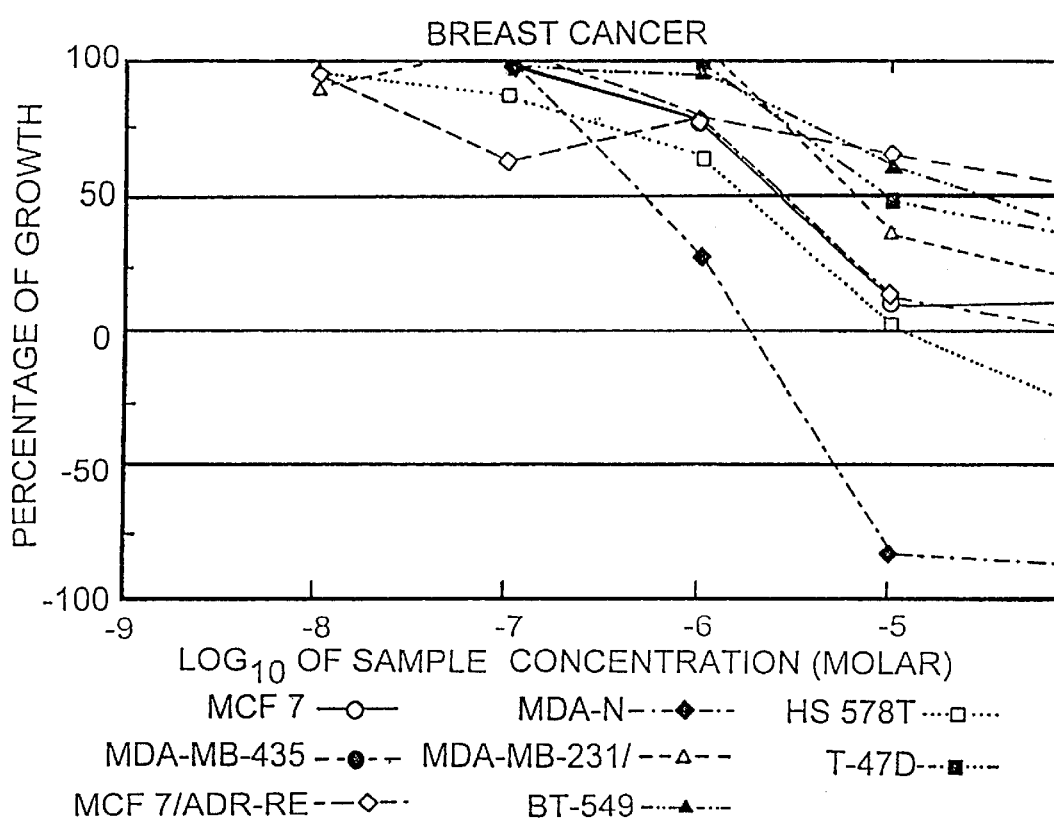
FIG. 18 is a graph plotting concentration of conjugate 2 versus percent growth of breast cancer cells.
Figure 19:
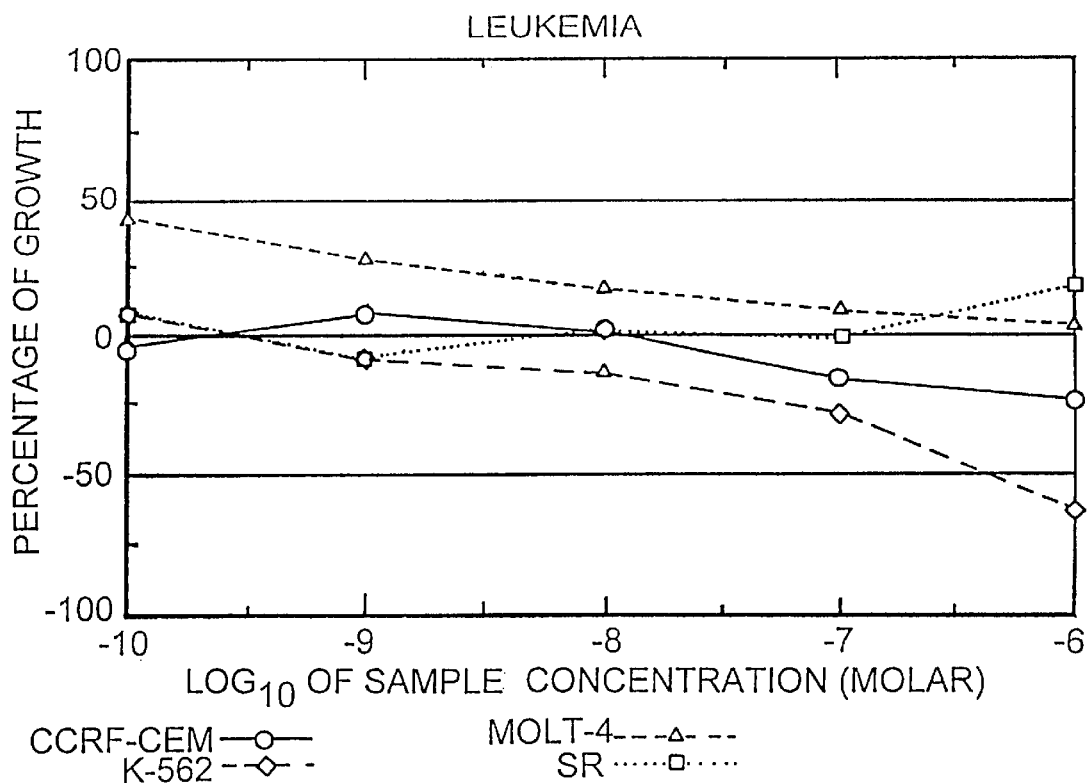
FIG. 19 is a graph plotting concentration of Taxol versus percent growth of leukemia cells.
Figure 20:
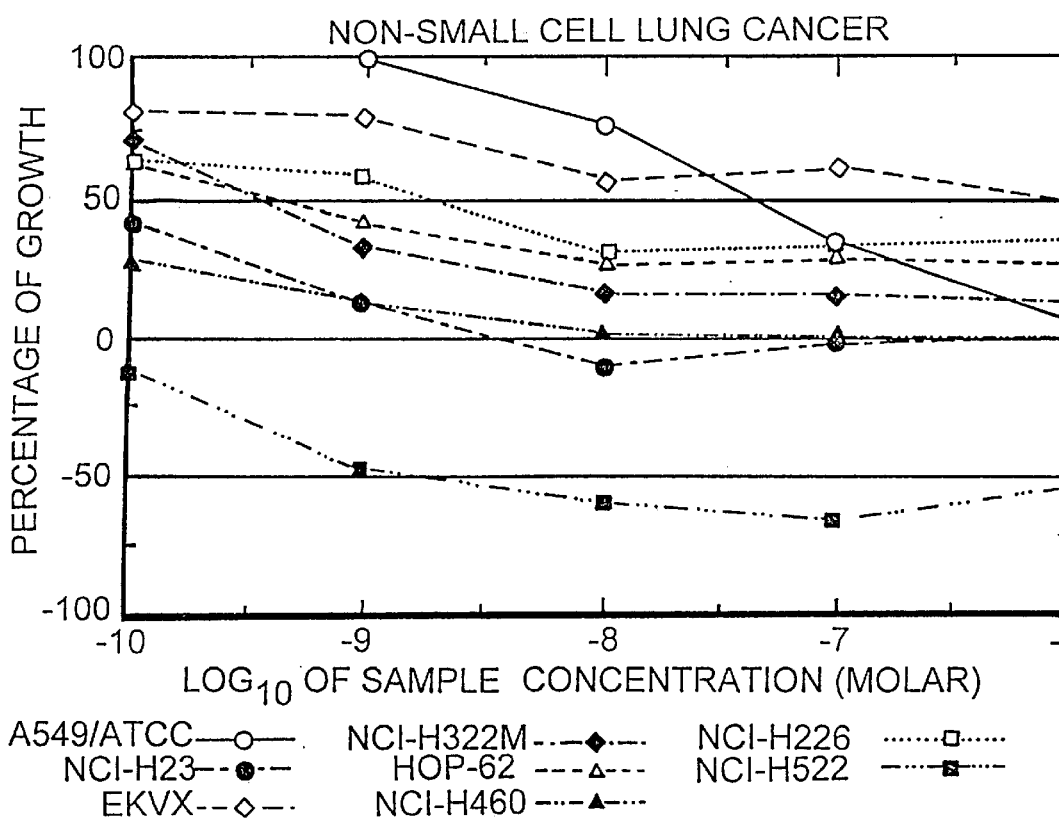
FIG. 20 is a graph plotting concentration of Taxol versus percent growth of non-small cell lung cancer cells.
Figure 21:
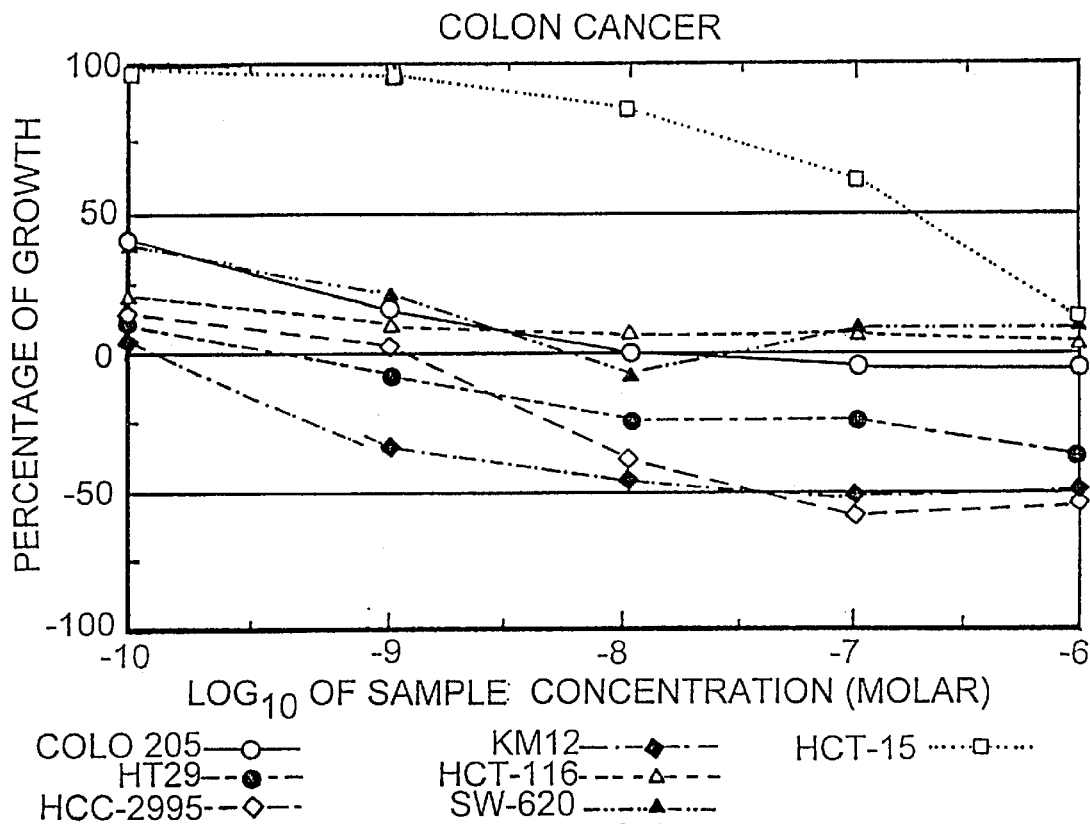
FIG. 21 is a graph plotting concentration of Taxol versus percent growth of colon cancer cells.
Figure 22:
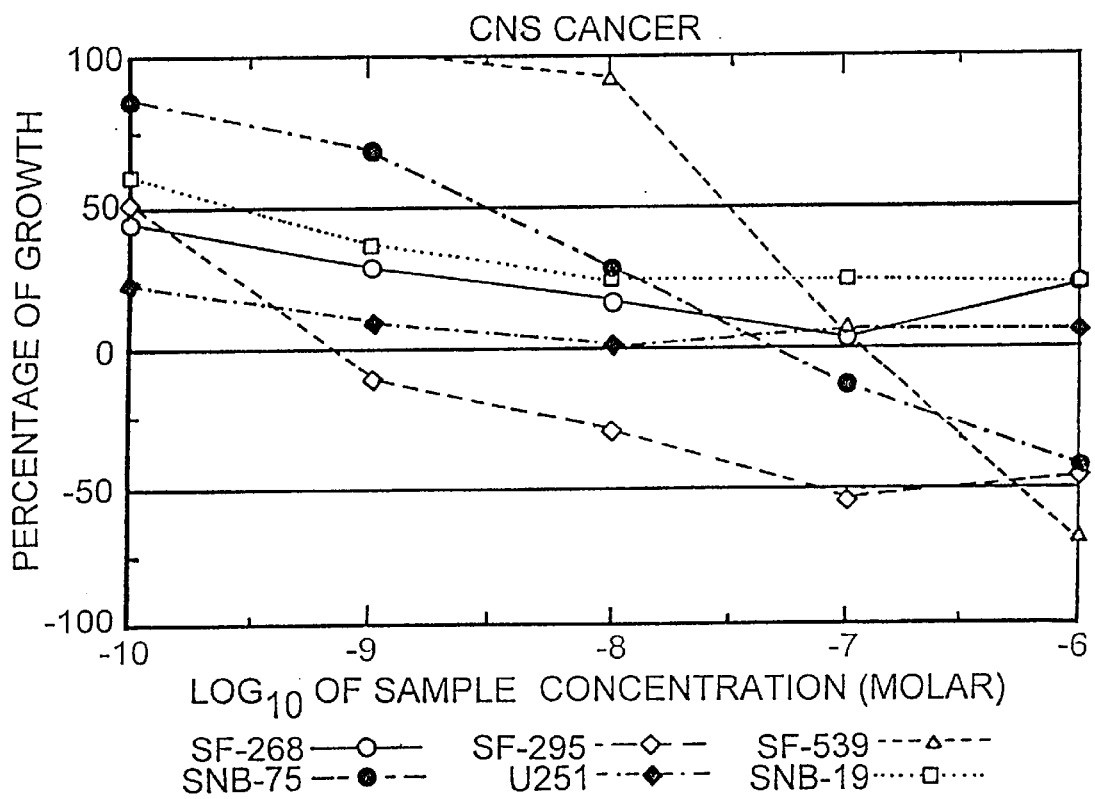
FIG. 22 is a graph plotting concentration of Taxol versus percent growth of CNS cancer cells.
Figure 23:
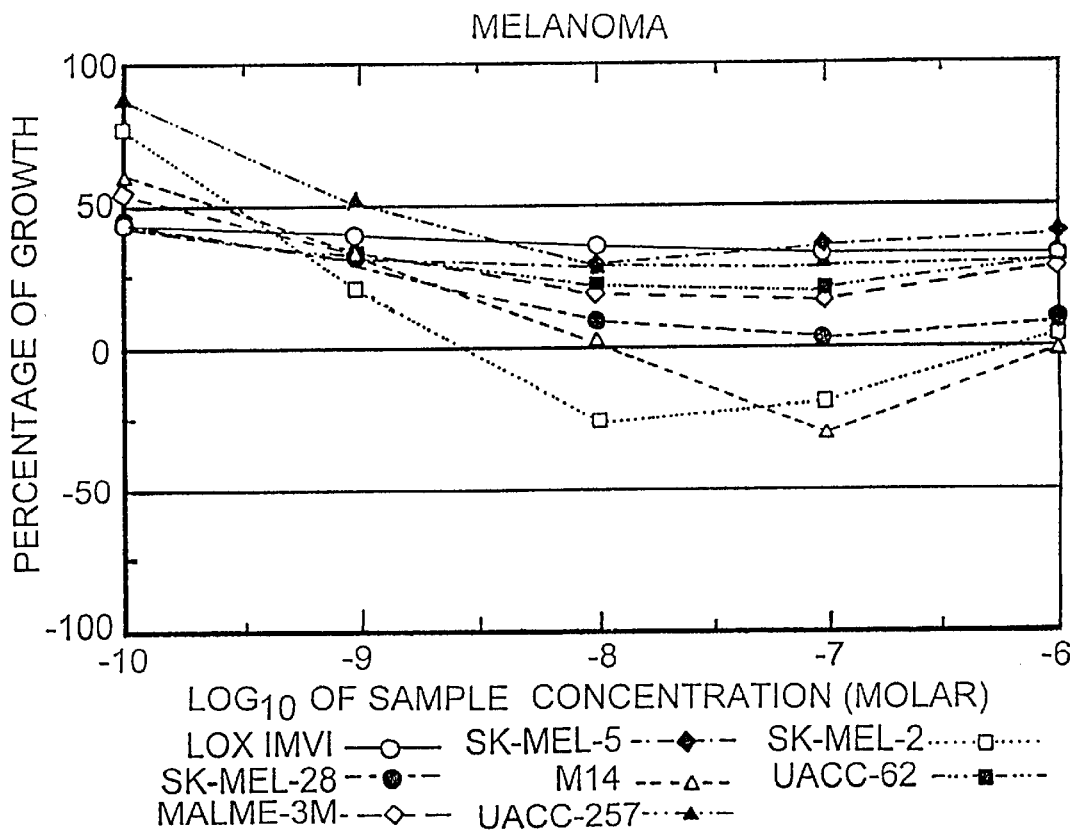
FIG. 23 is a graph plotting concentration of Taxol versus percent growth of melanoma cells.
Figure 24:
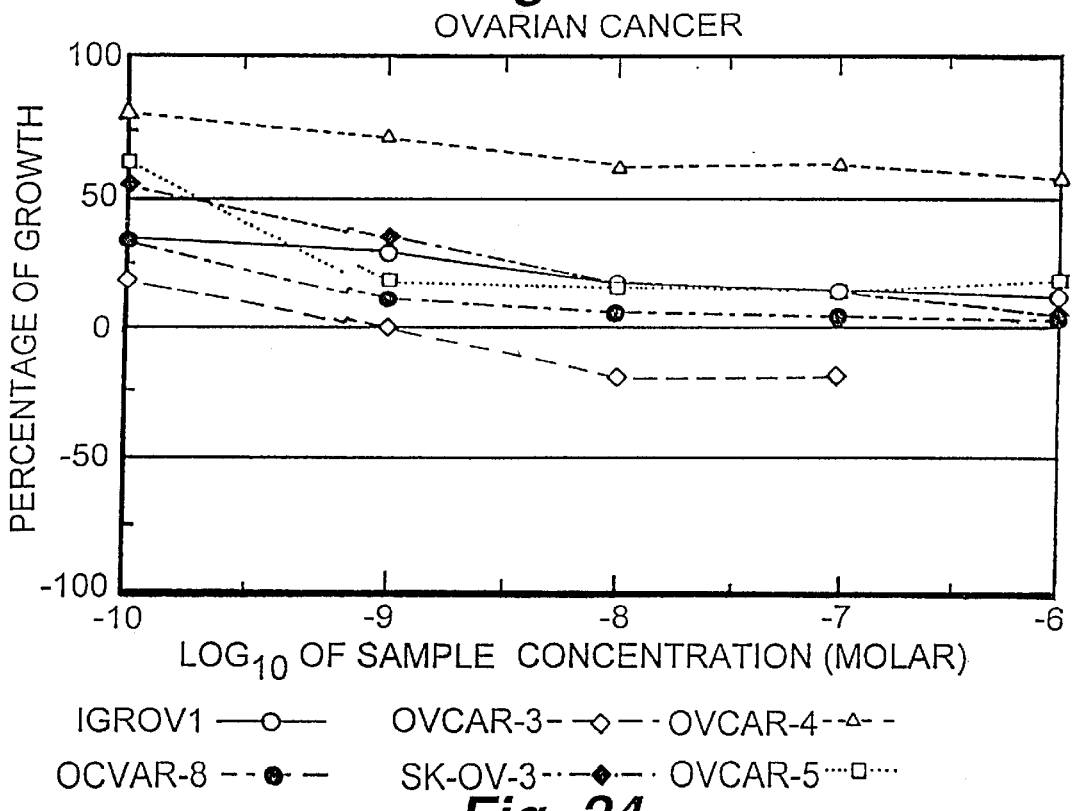
FIG. 24 is a graph plotting concentration of Taxol versus percent growth of ovarian cancer cells.
Figure 25:
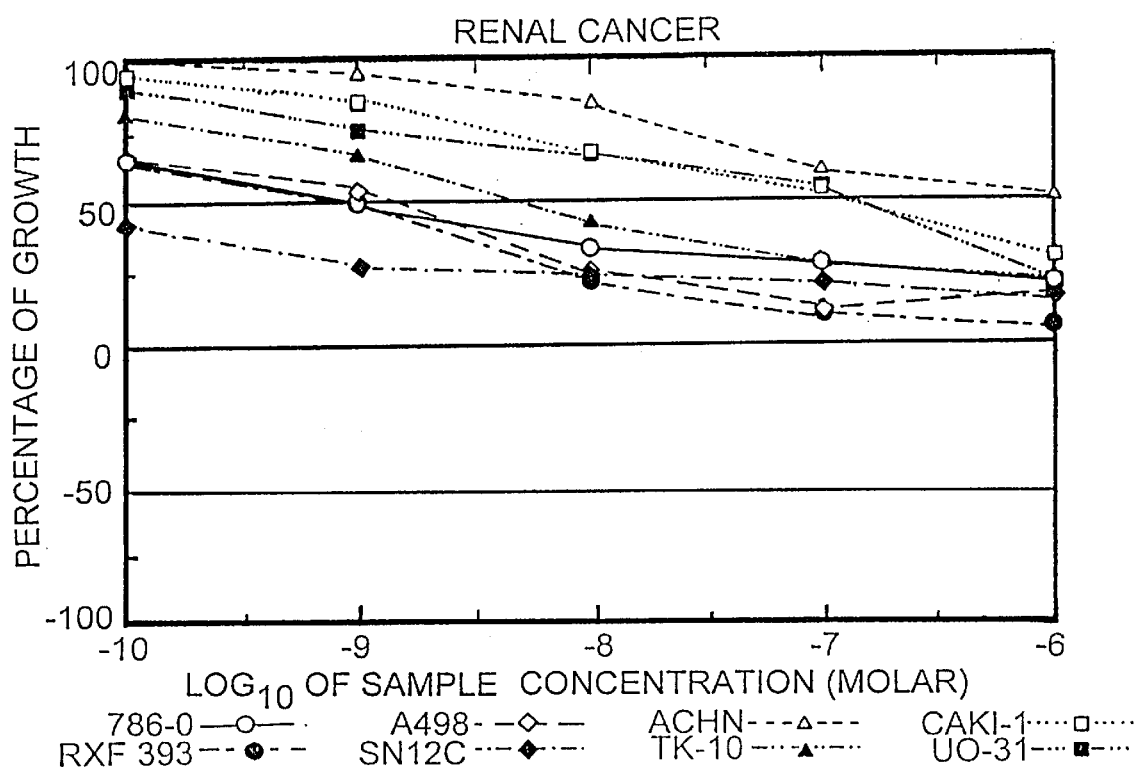
FIG. 25 is a graph plotting concentration of Taxol versus percent growth of renal cancer cells.
Figure 26:
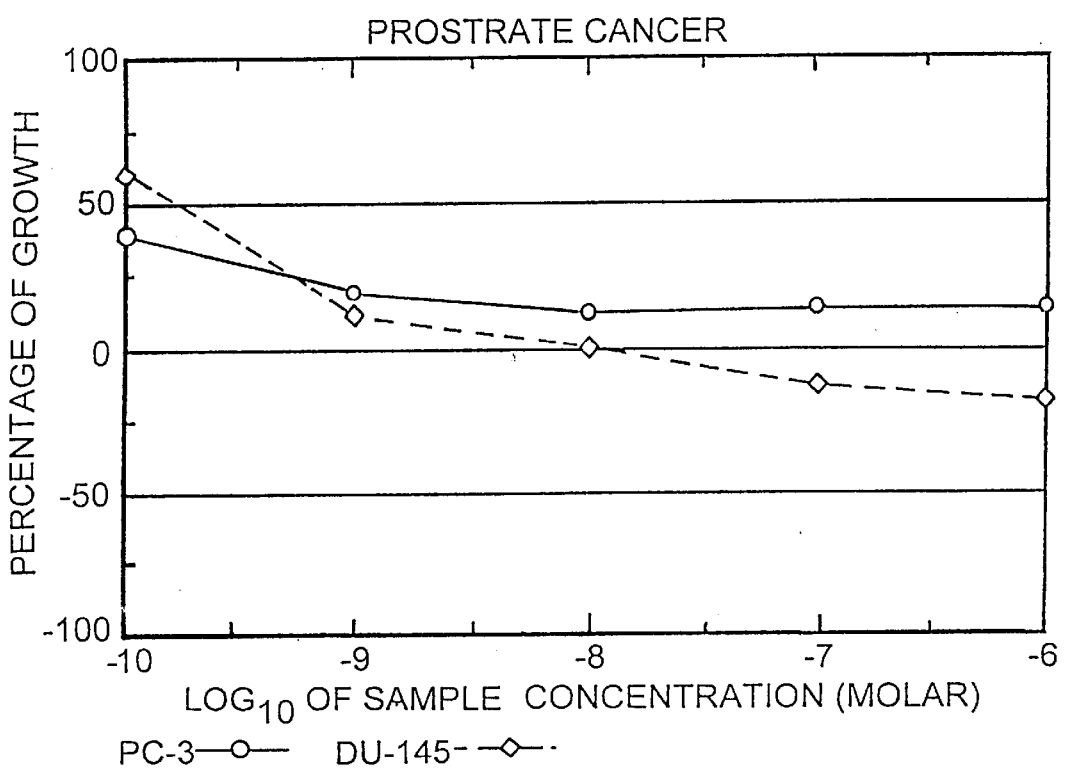
FIG. 26 is a graph plotting concentration of Taxol versus percent growth of prostate cancel cells.
Figure 27:
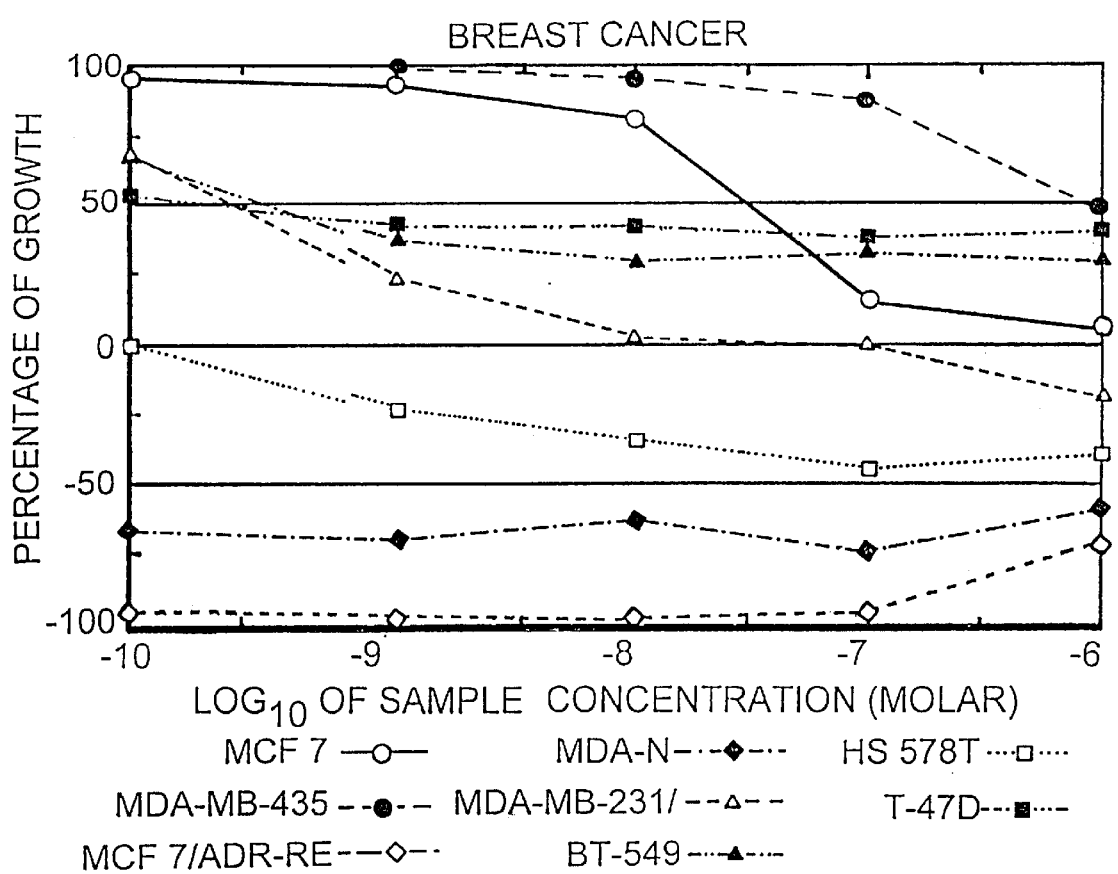
FIG. 27 is a graph plotting concentration of Taxol versus percent growth of breast cancer cells.

The activities of conjugates 1 and 2 were tested against 57 cancer cell lines. The results are presented in FIGS. 1–9 for conjugate 1, FIGS. 10–18 for conjugate 2 and FIGS. 19–27 for Taxol. To understand the data, reference is made to the guides provided by the NCI, excerpted as follows:

The Calculated Measurement of Effect: Percentage Growth (PG)

The measured effect of the compound on a cell line is currently calculated according to one or the other of the following two expressions:

If (Mean $OD_{test}$–Mean $OD_{tzero}$)≥0, then $PG=100\times$(Mean $OD_{test}$–Mean $OD_{tzero}$)/(Mean $OD_{ctrl}$–Mean $Od_{tzero}$)

If (Mean $OD_{test}$–Mean $OD_{tzero}$)<0, then $PG=100\times$(Mean $OD_{test}$–Mean $Od_{tzero}$)/Mean $Od_{tzero}$ Where:

| | |
|---|---|
| Mean $OD_{tzero}$ = | The average of optical density measurements of SRB-derived color just before exposure of cells to the test compound. |
| Mean $OD_{test}$ = | The average of optical density measurements of SRB-derived color after 48 hours exposure of cells to the test compound. |
| Mean $OD_{ctrl}$ = | The average of optical density measurements of SRB-derived color after 48 hours with no exposure of cells to the test compound. |

Experimental data was collected against each cell line. . . . Each concentration is expressed as the $\log_{10}$ (molar or $\mu$/g/ml). . . . The response parameters GI50, TGI, and LC50 are interpolated values representing the concentrations at which the PG is +50, 0, and −50, respectively. Sometimes these response parameters cannot be obtained by interpolation. If, for instance, all of the PGs in a given row exceed +50, then none of the three parameters can be obtained by interpolation. In such a case, the value given for each response parameter is the highest concentration tested. . . . This practice is extended similarly to the other possible situations where a response parameter cannot be obtained by interpolation.

Dose-Response Curves

The dose-response curve page of the data package is created by plotting the PGs against the $\log_{10}$ of the corresponding concentration for every cell line. The cell line curves are grouped by subpanel. Horizontal lines are provided at the PG values of +50, 0, and −50. The concentrations corresponding to points where the curves cross these lines are the GI50, TGI and LC50, respectively.

Several important distinctions are apparent from the data. Most important, the patterns of anticancer actively for conjugates 1 and 2 differ from that of Taxol. In one sense, conjugates 1 and 2 are effective anticancer agents against a more restricted set of cancer cell lines. For example, conjugates 1 and 2 were not very effective against any of the six leukemia cancer cell lines tested, whereas Taxol was somewhat effective against all four leukemia cell lines against which Taxol was tested. (See FIGS. 1, 10 and 19.)

The relative activity against members within a class of cancers also was altered. For example, at TGI (horizontal line at zero in the graphs), Taxol was more effective against non-small cell lung cancer line H522 than against H460 (by about 3 logs), whereas conjugates 1 and 2 were slightly more effective against H460 than H522. As another example, Taxol was least effective at TGI against CNSU251, whereas conjugate 1 was most effective against CNSU251 and conjugates 2 was also very effective against CNSU251(relative to other CNS cell lines). As a further example, Taxol was equivalent in activity toward MDA-N and MDA-MB-435 breast cancer cell lines at all concentrations tested, whereas conjugates 1 and 2 were more effective against MDA-N than MDA-MB-435 at all concentrations tested.

To further illustrate the differences in the activity of conjugates 1 and 2 versus that of Taxol, the NCI subjected the data to a statistical analysis designed by the NCI to reflect differences in the pattern of activity of anticancer agents. Conjugate 1 and conjugate 2 were determined to be statistically different in their pattern of activity versus Taxol in this unique measurement by the NCI.

It also is to be noted that, in general, conjugates 1 and 2 were one thousand to ten thousand times less potent than Taxol for many cell lines tested. This reduction in activity is important, especially since conjugates 1 and 2 maintained strong activity against some cell lines. Conjugates 1 and 2 will be sufficiently active against certain cell lines, but will have, on average, a substantially and disproportionately lower activity against other cell lines, reducing potential side effects. For example, the TGI for Taxol against CNS SF-539 is −6.95, and the TGI for conjugate 1 against this cell line is −5.13 and for conjugate 2 is −5.53. (In other words, the activity of the conjugates was reduced versus that of Taxol by less than 2 logs). The GI50 for Taxol against CNS SF 539 is −7.52, whereas the GI50s for conjugates 1 and 2 are −6.22 and −5.56, respectively (again less than 2 logs difference). In contrast, Taxol has a G150 for cell line CNSSF 268 of less than −10.0, whereas conjugates 1 and 2 have GI50s for CNSSF 268 of 5.36 and 5.28, respectively. This represents a reduction of activity in the conjugates vs. that of Taxol by at least about 5 logs activity! On average, the G150 for Taxol across all cell lines tested is at least −9.19. (It is probably much higher since concentrations less than −10 were not tested, and if Taxol was active at −10.0, −10 (instead of the actual lower value) was used in calculating the average of −9.19. There were 27 instances when this occurred.) The average GI50s for conjugates 1 and 2 , on the other hand, were 5.49 and 5.22, respectively. Therefore, the average difference in activity for Taxol vs. the conjugates is at least between 3 and 4 logs. Thus, the sharp reduction in the activity of the conjugates against many cell lines vs. a lesser reduction for other cell lines is expected to reduce the potential side effects of the conjugates versus those of Taxol at effective doses.

Cancers other than CNS, breast and colon cancer can be treated. For example, there was activity against non-small cell lung cancer cells, melanoma cells and ovarian cancer cells. However, the activity was relatively reduced and was extremely specific, limiting the utility of the conjugates for treating generally such cancers. In any event, cancer patients could be evaluated to determine if a conjugate is strongly active against the patient's cancer prior to selecting the conjugate as the anti-cancer agent of choice for that patient.

The foregoing experiments establish that DHA analogs have altered specificity versus that of Taxol for cancer cell lines. Because of this altered specificity, it also is clear that the conjugates themselves are gaining access into the target cells (as opposed to simply releasing Taxol into the environment outside of the cell). Thus, the DHA moiety appears to selectively target certain cell types as opposed to others. The ability of the conjugates to gain entry into the cells was unknown prior to the invention, and the ability of the DHA moiety to selectively target certain cell types was unexpected.

The same is true of DHA-Taxotere covalent conjugates, examples of which are presented below. Taxotere's synthesis has been reported extensively in the literature. One example is Kanazawa, A. et al., *J. Organic Chem.* 1994, Vol. 59, pp. 1238–1240.

EXAMPLE 4

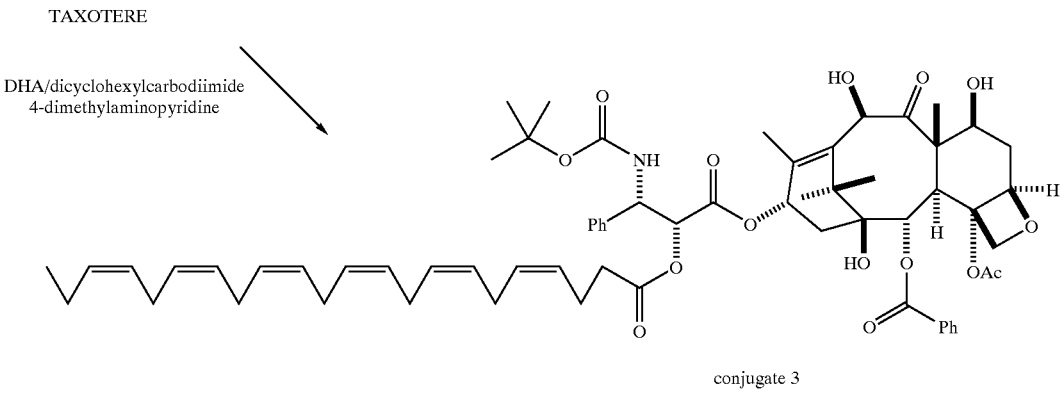

conjugate 3

A solution of Taxotere in methylene chloride under argon is mixed with 4-dimethylaminopyridine, dicyclohexylcarbodiimide, and DHA. The reaction mixture is stirred at ambient temperature. Radial chromatography of the residue is performed to produce Taxotere-DHA conjugate 3.

EXAMPLE 5

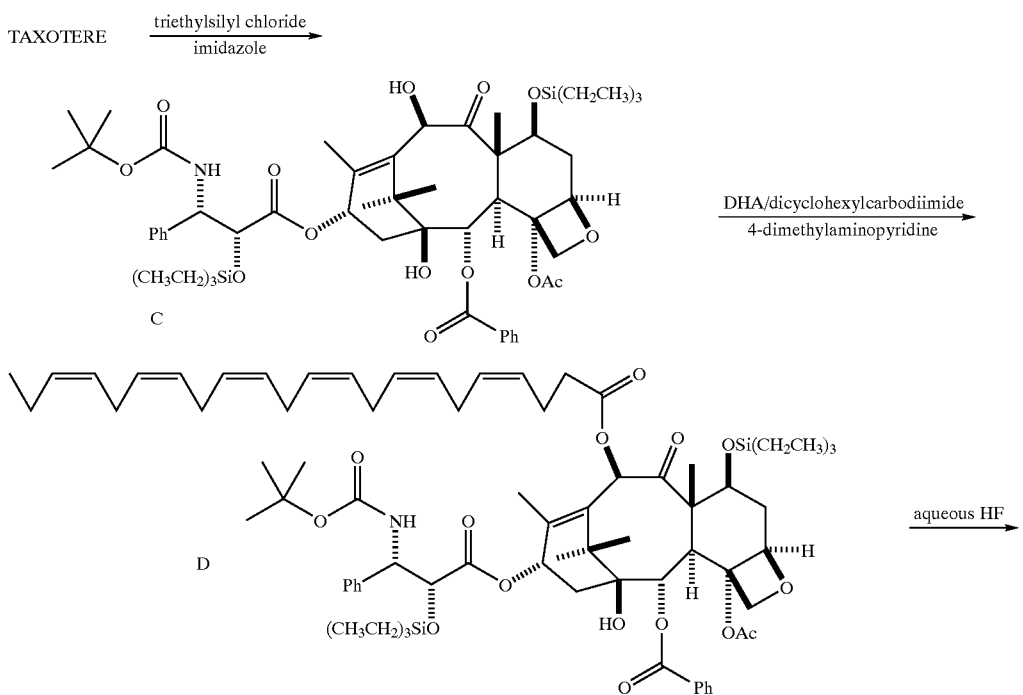

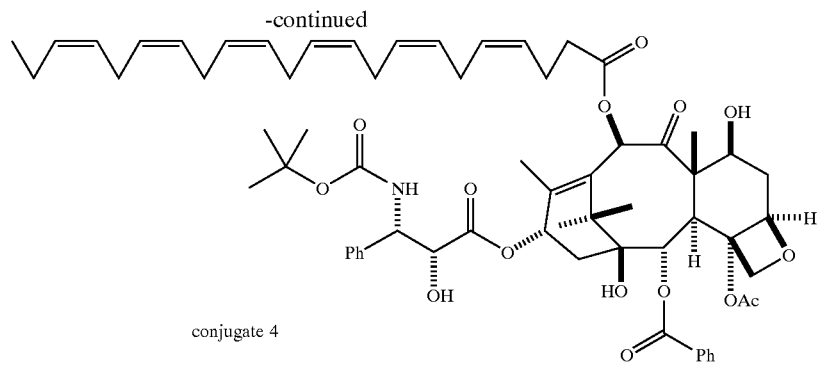

conjugate 4

A solution of Taxotere in dimethylformamide is mixed at ambient temperature under argon with imidazole and triethylsilyl chloride. The reaction mixture is stirred at ambient temperature, diluted with methylene chloride, washed with water, saturated acqueous'sodium chloride, dried, and concentrated. Radial chromatography of the residue is performed to produce intermediate C. A solution of intermediate C in methylene chloride is mixed at ambient temperature under argon with 4 dimethylaminopyridine, dicyclohexylcarbodiimide, and DHA. The reaction mixture is stirred at ambient temperature, diluted with ether, passed through celite, and concentrated. Radial chromatography of the residue is performed to produce intermediate D. A solution of intermediate D in acctonitrile at 0° C. under argon is mixed with 49% aqueous HF and the reaction mixture is stirred at the same temperature. After dilution with ether, the reaction mixture is washed with water, saturated aqueous sodium chloride, dried, and concentrated Radial chromatography of the residue is performed to produce Taxotere-DHA conjugate 4.

EXAMPLE 6

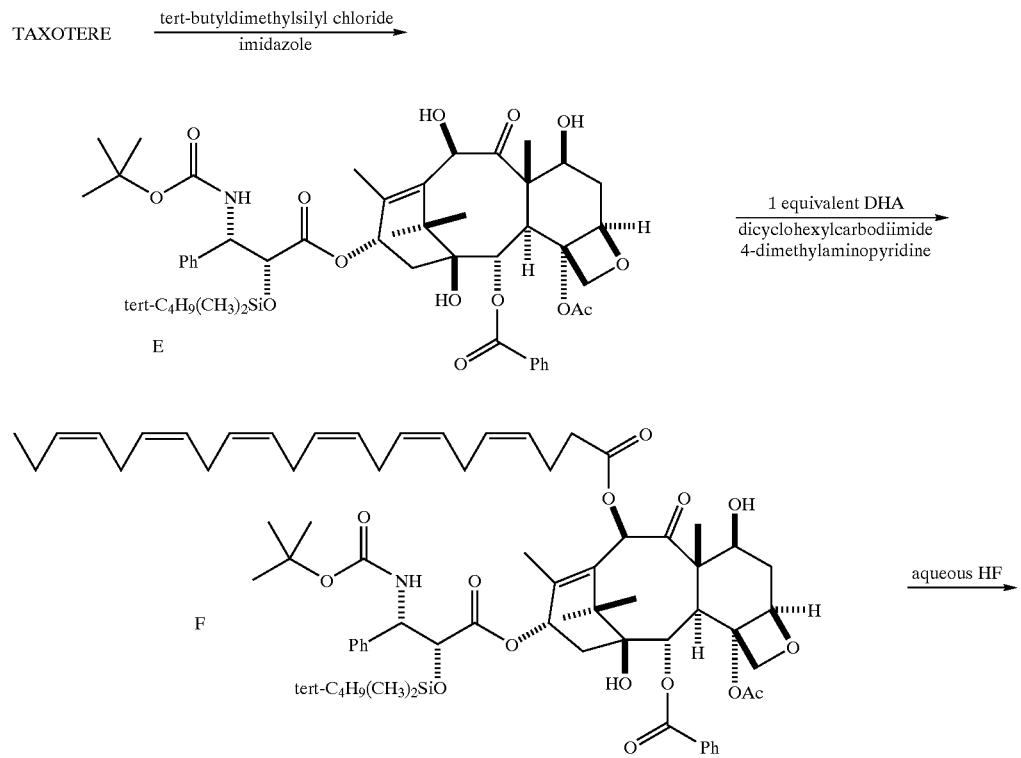

-continued

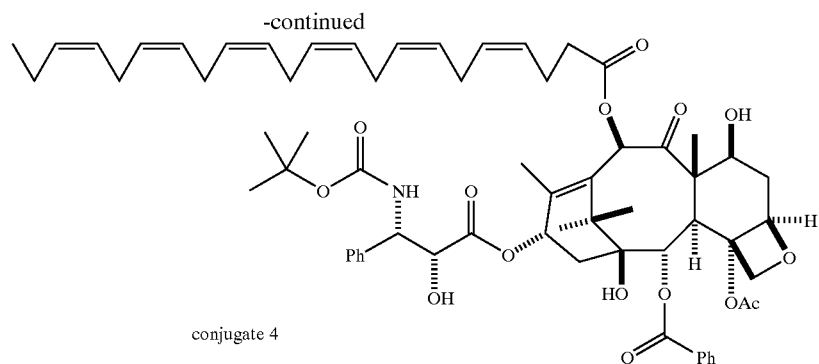

conjugate 4

A solution of Taxotere in dimethylformamide is mixed at ambient temperature under argon with imidazole and tert-butyldimethylsilyl chloride. The reaction mixture is stirred at ambient temperature, diluted with methylene chloride, washed with water, saturated aqueous sodium chloride, dried, and concentrated. Radial chromatography of the residue is performed to produce intermediate E. A solution of intermediate E in methylene chloride is mixed at ambient temperature under argon with 4-dimethylaminopyridine, dicyclohexylcarbodiimide, and 1 equivalent of DHA. The reaction mixture is stirred at ambient temperature, diluted with ether, passed through celite, and concentrated. Radial chromatography of the residue is performed to produce intermediate F. (Intermediate H also is obtained and used in Example 8 below) A solution of intermediate F in acetonitrile at 0° C. under argon is mixed with aqueous HF and the reaction mixture is stirred at the same temperature. After dilution with ether, the reaction mixture is washed with water, saturated aqueous sodium chloride. dried. and concentrated Radial chromatography of the residue is performed to produce Taxotere-DHA conjugate 4.

EXAMPLE 7

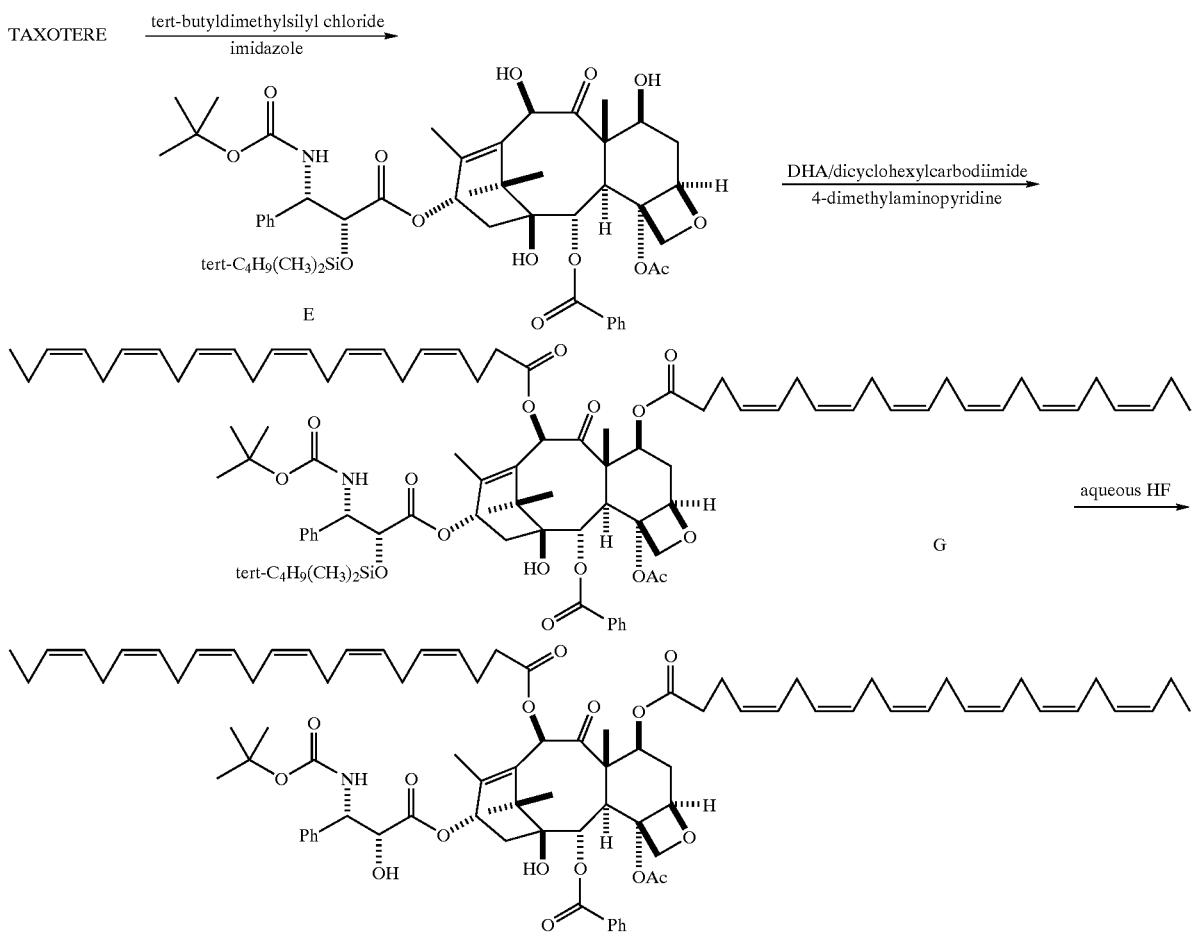

A solution of Taxotere in dimethylformamide is mixed at ambient temperature under argon with imidazole and tert-butyldimethylsilyl chloride. The reaction mixture is stirred at ambient temperature, diluted with methylene chloride, washed with water, saturated aqueous sodium chloride, dried, and concentrated. Radial chromatography of the residue is performed to produce intermediate E. A solution of intermediate E in methylene chloride is mixed at ambient temperature under argon with 4-dimethylaminopyridine, dicyclohexylcarbodiimide, and DHA. The reaction mixture is stirred at ambient temperature, diluted with ether, passed through celite, and concentrated. Radial chromatography of the residue is performed to produce intermediate G. A solution of intermediate G in acetonitrile at 0° C. under argon is mixed with aqueous HF and the reaction mixture is stirred at the same temperature. After dilution with ether, the reaction mixture is washed with water, saturated aqueous sodium chloride, dried, and concentrated. Radial chromatography of the residue is performed to produce Taxotere-DHA conjugate 5.

EXAMPLE 8 at ambient temperature, diluted with methylene chloride, washed with water, saturated aqueous sodium chloride, dried, and concentrated. Radial chromatography of the residue is performed to produce intermediate E. A solution of intermediate E in methylene chloride is mixed at ambient temperature under argon with 4-dimethylaminopyridine, dicyclohexylcarbodiimide, and 1 equivalent of DHA. The reaction mixture is stirred at ambient temperature, diluted with ether, passed through celite, and concentrated. Radial chromatography of the residue is performed to produce intermediate H (and intermediate F which was used above on Example 6. A solution of intermediate H in acetonitrile at 0° C. under argon is mixed with aqueous HF and the reaction mixture is stirred at the same temperature. After dilution with ether, the reaction mixture is washed with water, saturated aqueous sodium chloride, dried, and concentrated. Radial chromatography of the residue is performed to produce Taxotere-DHA conjugate 6.

DHA may be conjugated to virtually any drug compound or diagnostic agent and used according to the methods of the present invention so long as the pharmaceutical agent has a use outside of the central nervous system. Pharmaceutical

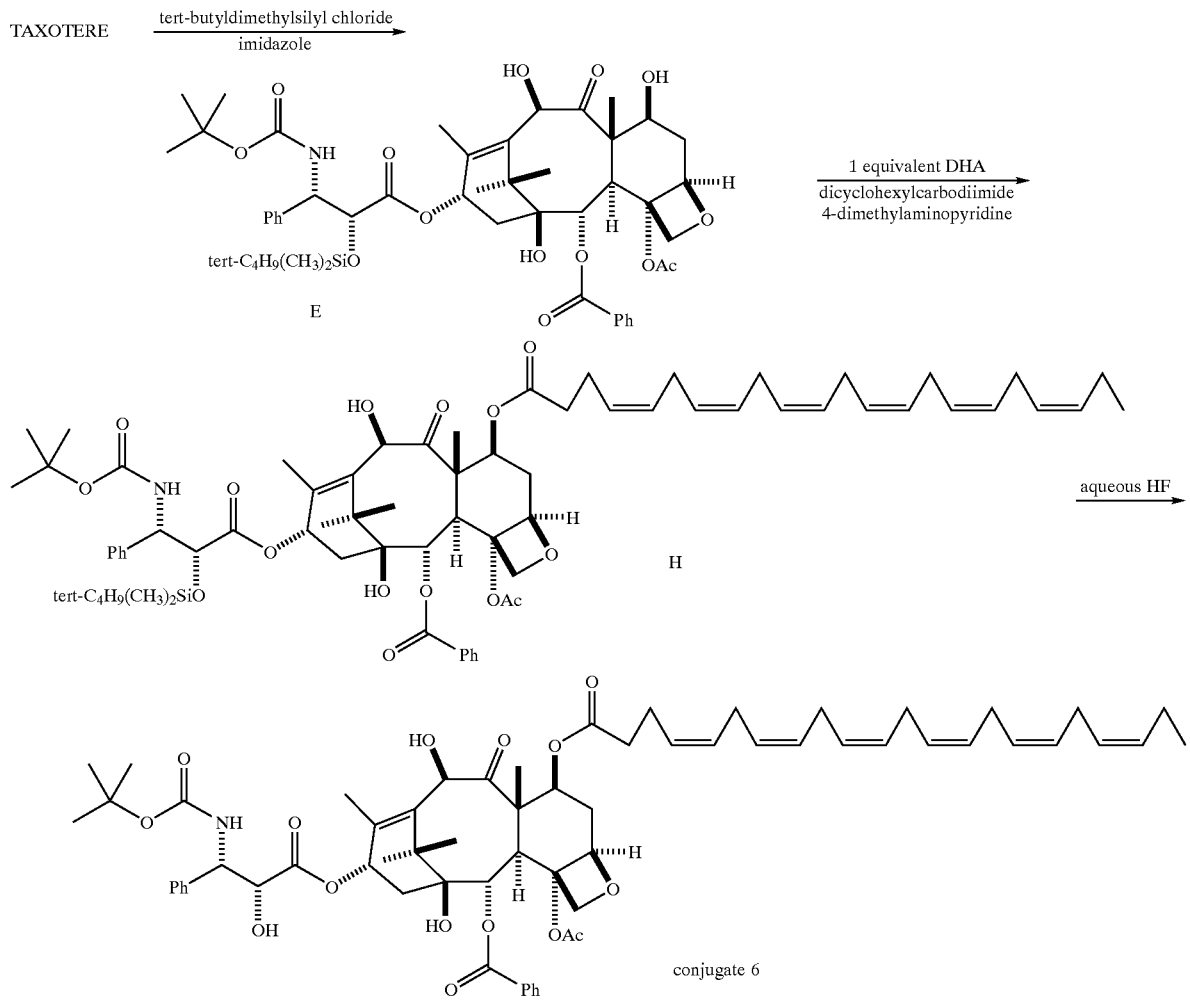

A solution of taxotere in dimethylformamide is mixed at ambient temperature under argon with imidazole and tert-butyldimethylsilyl chloride. The reaction mixture is stinted agents include the following categories and specific examples. It is not intended that the category be limited by the specific examples. Those of ordinary skill in the art will be able to identify readily those pharmaceutical agents that have utility outside of the central nervous system. Those of ordinary skill in the art will recognize also numerous other compounds that fall within the categories and that are useful according to the invention.

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; Tipredane.

Adrenocortical suppressant: Aminoglutethimide; Trilostane.

Alcohol deterrent: Disulfiram.

Aldosterone antagonist: Canrenoate Potassium; Canrenone; Dicirenone; Mexrenoate Potassium; Prorenoate Potassium; Spironolactone.

Amino acid: Alanine; Aspartic Acid; Cysteine Hydrochloride; Cystine; Histidine; Isoleucine; Leucine; Lysine; Lysine Acetate; Lysine Hydrochloride; Methionine; Phenylalanine; Proline; Serine; Threonine; Tryptophan; Tyrosine; Valine.

Ammonia detoxicant: Arginine: Arginine Glutamate; Arginine Hydrochloride.

Anabolic: Bolandiol Dipropionate; Bolasterone; Boldenone Undecylenate; Bolenol; Bolmantalate; Ethylestrenol; Methenolone Acetate; Methenolone Enanthate; Mibolerone; Nandrolone Cyclotate; Norbolethone; Pizotyline; Quinbolone; Stenbolone Acetate; Tibolone; Zeranol.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Androgen: Fluoxymesterone; Mesterolone; Methyltestosterone; Nandrolone Decanoate; Nandrolone Phenpropionate; Nisterime Acetate; Oxandrolone; Oxymetholone; Silandrone; Stanozolol; Testosterone; Testosterone Cypionate; Testosterone Enanthate; Testosterone Ketolaurate; Testosterone Phenylacetate; Testosterone Propionate; Trestolone Acetate.

Anesthesia, adjunct to: Sodium Oxybate.

Anesthetic: Aliflurane; Benoxinate Hydrochloride; Benzocaine; Biphenamine Hydrochloride; Bupivacaine Hydrochloride; Butamben; Butamben Picrate; Chloroprocaine Hydrochloride; Cocaine; Cocaine Hydrochloride; Cyclopropane; Desflurane; Dexivacaine; Diaminocaine Cyclamate; Dibucaine; Dibucaine Hydrochloride; Dyclonine Hydrochloride; Enflurane; Ether; Ethyl Chloride; Etidocaine; Etoxadrol Hydrochloride; Euprocin Hydrochloride; Fluroxene; Halothane; Isobutamben; Isoflurane; Ketamine Hydrochloride; Levoxadrol Hydrochloride; Lidocaine; Lidocaine Hydrochloride; Mepivacaine Hydrochloride; Methohexital Sodium; Methoxyflurane; Midazolam Hydrochloride; Midazolam Maleate; Minaxolone; Nitrous Oxide; Norflurane; Octodrine; Oxethazaine; Phencyclidine Hydrochloride; Pramoxine Hydrochloride; Prilocaine Hydrochloride; Procaine Hydrochloride; Propanidid; Proparacaine Hydrochloride; Propofol; Propoxycaine Hydrochloride; Pyrrocaine; Risocaine; Rodocaine; Roflurane; Salicyl Alcohol; Sevoflurane; Teflurane; Tetracaine; Tetracaine Hydrochloride; Thiamylal; Thiamylal Sodium; Thiopental Sodium; Tiletamine Hydrochloride; Zolamine Hydrochloride.

Anorectic compounds including dexfenfluramine.

Anorexic: Aminorex; Amphecloral; Chlorphentermine Hydrochloride; Clominorex; Clortermine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phenmetrazine Hydrochloride; Phentermine; Sibutramine Hydrochloride.

Antagonist: Atipamezole; Atosiban; Bosentan; Cimetidine; Cimetidine Hydrochloride; Clentiazem Maleate; Detirelix Acetate; Devazepide; Donetidine; Etintidine Hydrochloride; Famotidine; Fenmetozole Hydrochloride; Flumazenil; Icatibant Acetate; Icotidine; Isradipine; Metiamide; Nadide; Nalmefene; Nalmexone Hydrochloride; Naloxone Hydrochloride; Naltrexone; Nilvadipine; Oxilorphan; Oxmetidine Hydrochloride; Oxmetidine Mesylate; Quadazocine Mesylate; Ranitidine; Ranitidine Bismuth Citrate; Ranitidine Hydrochloride; Sufotidine; Teludipine Hydrochloride; Tiapamil Hydrochloride; Tiotidine; Vapiprost Hydrochloride; Zaltidine Hydrochloride.

Anterior pituitary activator: Epimestrol.

Anterior pituitary suppressant: Danazol.

Anthelmintic: Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; Piperazine; Piperazine Citrate; Piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Triclofenol Piperazine; Vincofos; Zilantel.

Anti-acne: Adapalene; Erythromycin Salnacedin; Inocoterone Acetate.

Anti-adrenergic: Acebutolol; Alprenolol Hydrochloride; Atenolol; Bretylium Tosylate; Bunolol Hydrochloride; Carteolol Hydrochloride; Celiprolol Hydrochloride; Cetamolol Hydrochloride; Cicloprolol Hydrochloride; Dexpropranolol Hydrochloride; Diacetolol Hydrochloride; Dihydroergotamine Mesylate; Dilevalol Hydrochloride; Esmolol Hydrochloride; Exaprolol Hydrochloride; Fenspiride Hydrochloride; Flestolol Sulfate; Labetalol Hydrochloride; Levobetaxolol Hydrochloride; Levobunolol Hydrochloride; Metalol Hydrochloride; Metoprolol; Metoprolol Tartrate; Nadolol; Pamatolol Sulfate; Penbutolol Sulfate; Phentolamine Mesylate; Practolol; Propranolol Hydrochloride; Proroxan Hydrochloride; Solypertine Tartrate; Sotalol Hydrochloride; Timolol; Timolol Maleate; Tiprenolol Hydrochloride; Tolamolol; Zolertine Hydrochloride.

Anti-allergic: Amlexanox; Astemizole; Azelastine Hydrochloride; Eclazolast; Minocromil; Nedocromil; Nedocromil Calcium; Nedocromil Sodium; Nivimedone Sodium; Pemirolast Potassium; Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; Tixanox.

Anti-amebic: Berythromycin; Bialamicol Hydrochloride; Chloroquine; Chloroquine Hydrochloride; Chloroquine Phosphate; Clamoxyquin Hydrochloride; Clioquinol; Emetine Hydrochloride; Iodoquinol; Paromomycin Sulfate; Quinfamide; Symetine Hydrochloride; Teclozan; Tetracycline; Tetracycline Hydrochloride.

Anti-androgen: Benorterone; Cioteronel; Cyproterone Acetate; Delmadinone Acetate; Oxendolone; Topterone; Zanoterone.

Anti-anemic: Epoetin Alfa; Epoetin Beta; Ferrous Sulfate, Dried; Leucovorin Calcium.

Anti-anginal: Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; Verapamil Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; Zalospirone Hydrochloride.

Anti-arthritic: Lodelaben.

Anti-asthmatic: Ablukast; Ablukast Sodium; Azelastine Hydrochloride; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Repirinast; Ritolukast; Sulukast; Tetrazolast Meglumine; Tiaramide Hydrochloride; Tibenelast Sodium; Tomelukast; Tranilast; Verlukast; Verofylline; Zarirlukast.

Anti-atherosclerotic: Mifobate; Timefurone.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anticholelithic: Monoctanoin.

Anticholelithogenic: Chenodiol; Ursodiol.

Anticholinergic: Alverinc Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; Tropicamide.

Anticoagulant: Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; Warfarin Sodium.

Anticoccidal: Maduramicin.

Anticonvulsant: Albutoin; Ameltolide; Atolide; Buramate; Carbamazepine; Cinromide; Citenamide; Clonazepam; Cyheptamide; Dezinamide; Dimethadione; Divalproex Sodium; Eterobarb; Ethosuximide; Ethotoin; Flurazepam Hydrochloride; Fluzinamide; Fosphenytoin Sodium; Gabapentin; Ilepcimide; Lamotrigine; Magnesium Sulfate; Mephenytoin; Mephobarbital; Methetoin; Methsuximide; Milacemide Hydrochloride; Nabazenil; Nafimidone Hydrochloride; Nitrazepam; Phenacemide; Phenobarbital; Phenobarbital Sodium; Phensuximide; Phenytoin; Phenytoin Sodium; Primidone; Progabide;

Ralitoline; Remacemide Hydrochloride; Ropizine; Sabeluzole; Stiripentol; Sulthiame; Thiopental Sodium; Tiletamine Hydrochloride; Topiramate; Trimethadione; Valproate Sodium; Valproic Acid; Vigabatrin; Zoniclezole Hydrochloride; Zonisamide.

Antidepressant: Adatanserin Hydrochloride; Adinazolam; Adinazolam Mesylate; Alaproclate; Aletamine Hydrochloride; Amedalin Hydrochloride; Amitriptyline Hydrochloride; Amoxapine; Aptazapine Maleate; Azaloxan Fumarate; Azepindole; Azipramine Hydrochloride; Bipenamol Hydrochloride; Bupropion Hydrochloride; Butacetin; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fehmetozole Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Milacemide Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pizotyline; Pridefine Hydrochloride; Prolintane Hydrochloride; Protriptyline Hydrochloride; Quipazine Maleate; Rolicyprine; Seproxetine Hydrochloride; Sertraline Hydrochloride; Sibutramine Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine; Trimipramine Maleate; Venlafaxine Hydrochloride; Viloxazine Hydrochloride; Zimeldine Hydrochloride; Zometapine.

Antidiabetic: Acetohexamide; Buformin; Butoxamine Hydrochloride; Camiglibose; Chlorpropamide; Ciglitazone; Englitazone Sodium; Etoformin Hydrochloride; Gliamilide; Glibomuride; Glicetanile Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Seglitide Acetate; Tolazamide; Tolbutamide; Tolpyrramide; Troglitazone; Zopolrestat.

Antidiarrheal: Rolgamidine, Diphenoxylate hydrochloride (Lomotil), Metronidazole (Flagyl), Methylprednisolone (Medrol), Sulfasalazine (Azulfidine).

Antidiuretic: Argipressin Tannate; Desmopressin Acetate; Lypressin.

Antidote: Dimercaprol; Edrophonium Chloride; Fomepizole; Leucovorin Calcium; Levoleucovorin Calcium; Methylene Blue; Protamine Sulfate.

Antidyskinetic: Selegiline Hydrochloride.

Anti-emetic: Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Fludorex; Flumeridone; Galdansetron Hydrochloride; Granisetron; Granisetron Hydrochloride; Lurosetron Mesylate; Meclizine Hydrochloride; Metoclopramide Hydrochloride; Metopimazine; Ondansetron Hydrochloride; Pancopride; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; Zacopride Hydrochloride.

Anti-epileptic: Felbamate; Loreclezole; Tolgabide.

Anti-estrogen: Clometherone; Delmadinone Acetate; Nafoxidine Hydrochloride; Nitromifene Citrate; Raloxifene Hydrochloride; Tamoxifen Citrate; Toremifene Citrate; Trioxifene Mesylate.

Antifibrinolytic: Nafamostat Mesylate.

Antifungal: Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; Zinoconazole Hydrochloride.

Antiglaucoma agent: Alprenoxime Hydrochloride; Colforsin; Dapiprazole Hydrochloride; Dipivefrin Hydrochloride; Naboctate Hydrochloride; Pilocarpine; Pirnabine.

Antihemophilic: Antihemophilic Factor.

Antihemorrhagic: Poliglusam.

Antihistaminic: Acrivastine; Antazoline Phosphate; Astemizole; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cinnarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylaine Succinate; Ebastine; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Telfenadine; Tripelennamine Citrate; Tripelennamine Hydrochloride; Triprolidine Hydrochloride; Zolamine Hydrochloride.

Antihyperlipidemic: Cholestyramine Resin; Clofibrate; Colestipol Hydrochloride; Crilvastatin; Dalvastatin; Dextrothyroxine Sodium; Fluvastatin Sodium; Gemfibrozil; Lecimibide; Lovastatin; Niacin; Pravastatin Sodium; Probucol; Simvastatin; Tiqueside; Xenbucin.

Antihyperlipoproteinemic: Acifran; Beloxamide; Bezafibrate; Boxidine; Butoxamine Hydrochloride; Cetaben Sodium; Ciprofibrate; Gemcadiol; Halofenate; Lifibrate; Meglutol; Nafenopin; Pimetine Hydrochloride; Theofibrate; Tibric Acid; Treloxinate.

Antihypertensive: Alfuzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolapril Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutarnate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Antihypotensive: Ciclafrine Hydrochloride; Midodrine Hydrochloride.

Anti-infective: Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax), Norfloxacin (Noroxin); Cefoxitin (Mefoxin); Cefuroxime axetil (Ceftin); Ciprofloxacin (Cipro).

Anti-infective, topical: Alcohol; Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol, Domiphen Bromide; Fenticlor; Fludazonium Chloride; Fuchsin, Basic; Furazolidone; Gentian Violet; Halquinols; Hexachlorophene: Hydrogen Peroxide; Ichtharmol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal: Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; -Dexamethasone Dipropionate; Diclofenac Potassium; Diclofenac Sodium; Diflorasone Diacetate; -Diflumidone Sodium; Diflunisal; Difluprednate; Diftalone; Dimethyl Sulfoxide; Drocinonide; Endrysone; Enlimomab Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone;

Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antikeratinizing agent: Doretinel; Linarotene; Pelretin.

Antimalarial: Acedapsone; Amodiaquine Hydrochloride; Amquinate; Arteflene; Chloroquine; Chloroquine Hydrochloride; Chloroquine Phosphate; Cycloguanil Pamoate; Enpiroline Phosphate; Halofantrine Hydrochloride; Hydroxychloroquine Sulfate; Mefloquine Hydrochloride; Menoctone; Mirincamycin Hydrochloride; Primaquine Phosphate; Pyrimethamine; Quinine Sulfate; Tebuquine.

Antimicrobial: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine.

Antimigraine: Dolasetron Mesylate; Naratriptan Hydrochloride; Sergolexole Maleate; Sumatriptan Succinate; Zatosetron Maleate.

Antimitotic: Podofilox.

Antimycotic: Amorolfine.

Antinauseant: Buclizine Hydrochloride; Cyclizine Lactate; Naboctate Hydrochloride.

Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretanine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Antineutropenic: Filgrastim; Lenograstim; Molgramostim; Regramostim; Sargramostim.

Antiobsessional agent: Fluvoxamine Maleate.

Antiparasitic: Abamectin; Clorsulon; Ivermectin.

Antiparkinsonian: Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride.

Antiperistaltic: Difenoximide Hydrochloride; Difenoxin; Diphenoxylate Hydrochloride; Fluperamide; Lidamidine Hydrochloride; Loperamide Hydrochloride; Malethamer; Nufenoxole; Paregoric.

Antipneumocystic: Atovaquone.

Antiproliferative agent: Piritrexim Isethionate.

Antiprostatic hypertrophy: Sitogluside.

Antiprotozoal: Amodiaquine; Azanidazole; Bamnidazole; Carnidazole; Chlortetracycline Bisulfate; Chlortetracycline Hydrochloride; Flubendazole; Flunidazole; Halofuginone Hydrobromide; Imidocarb Hydrochloride; Ipronidazole; Metronidazole; Misonidazole; Moxnidazole; Nitarsone; Partricin; Puromycin; Puromycin Hydrochloride; Ronidazole; Sulnidazole; Tinidazole.

Antipruritic: Cyproheptadine Hydrochloride; Methdilazine; Methdilazine Hydrochloride; Trimeprazine Tartrate.

Antipsoriatic: Acitrelin; Anthralin; Azaribine; Calcipotriene; Cycloheximide; Enazadrem Phosphate; Etretinate; Liarozole Fumarate; Lonapalene; Tepoxalin.

Antipsychotic: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirlene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; Ziprasidone Hydrochloride.

Antirheumatic: Auranofin; Aurothioglucose; Bindarit; Lobenzarit Sodium; Phenylbutazone; Pirazolac; Prinomide Tromethamine; Seprilose.

Antischistosomal: Becanthone Hydrochloride; Hycanthone; Lucanthone Hydrochloride; Niridazole; Oxamniquine; Pararosaniline Pamoate; Teroxalene Hydrochloride.

Antiseborrheic: Chloroxine; Piroctone; Piroctone Olamine; Resorcinol Monoacetate.

Antisecretory: Arbaprostil; Deprostil; Fenoctimine Sulfate; Octreotide, Octreotide Acetate; Omeprazole Sodium; Rioprostil; Trimoprostil.

Antispasmodic: Stilonium Iodide; Tizanidine Hydrochloride.

Antithrombotic: Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Trifenagrel.

Antitussive: Benzonatate; Butamirate Citrate; Chlophedianol Hydrochloride; Codeine Polistirex; Codoxime; Dextromethorphan; Dextromethorphan Hydrobromide; Dextromethorphan Polistirex; Ethyl Dibunate; Guaiapate; Hydrocodone Bitartrate; Hydrocodone Polistirex; Levopropoxyphene Napsylate; Noscapine; Pemerid Nitrate; Pipazethate; Suxemerid Sulfate.

Anti-ulcerative: Aceglutamide Aluminum; Cadexomer Iodine; Cetraxate Hydrochloride; Enisoprost; Isotiquimide; Lansoprazole; Lavoltidine Succinate; Misoprostol; Nizatidine; Nolinium Bromide; Pantoprazole; Pifarnine; Pirenzepine Hydrochloride; Rabeprazole Sodium; Remiprostol; Roxatidine Acetate Hydrochloride; Sucralfate; Sucrosofate Potassium; Tolimidone.

Anti-urolithic: Cysteamine; Cysteamine Hydrochloride; Tricitrates.

Antiviral: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Appetite suppressant: Dexfenfluramine Hydrochloride; Phendimetrazine Tartrate; Phentermine Hydrochloride.

Benign prostatic hyperplasia therapy agent: Tamsulosin Hydrochloride.

Blood glucose regulators: Human insulin; Glucagon; Tolazamide; Tolbutamide; Chloropropamide; Acetohexamide and Glipizide.

Bone resorption inhibitor: Alendronate Sodium; Etidronate Disodium; Pamidronate Disodium.

Bronchodilator: Albuterol; Albuterol Sulfate; Azanator Maleate; Bamifylline Hydrochloride; Bitolterol Mesylate; Butaprost; Carbuterol Hydrochloride; Clorprenaline Hydrochloride; Colterol Mesylate; Doxaprost; Doxofylline; Dyphylline; Enprofylline; Ephedrine; Ephedrine Hydrochloride; Fenoterol; Fenprinast Hydrochloride; Guaithylline; Hexoprenaline Sulfate; Hoquizil Hydrochloride; Ipratropium Bromide; Isoetharine; Isoetharine Hydrochloride; Isoetharine Mesylate; Isoproterenol Hydrochloride; Isoproterenol Sulfate; Metaproterenol Polistirex; Metaproterenol Sulfate; Nisbuterol Mesylate; Oxtriphylline; Picumeterol Fumarate; Piquizil Hydrochloride; Pirbuterol Acetate; Pirbuterol Hydrochloride; Procaterol Hydrochloride; Pseudoephedrine Sulfate; Quazodine; Quinterenol Sulfate; Racepinephrine; Racepinephrine Hydrochloride; Reproterol Hydrochloride; Rimiterol Hydrobromide; Salmeterol; Salmeterol Xinafoate; Soterenol Hydrochloride; Sulfonterol Hydrochloride; Suloxifen Oxalate; Terbutaline Sulfate; Theophylline; Xanoxate Sodium; Zindotrine; Zinterol Hydrochloride.

Carbonic anhydrase inhibitor: Acetazolamide; Acetazolamide Sodium, Dichlorphenamide; Dorzolamide Hydrochloride; Methazolamide; Sezolamide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Butoprozine Hydrochloride; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride;

Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; Transcainide.

Cardioprotectant: Dexrazoxane; Draflazine.

Cardiotonic: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; Vesnarinone.

Cardiovascular agent: Dopexamine; Dopexamine Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Cholinergic agonist: Xanomeline; Xanomeline Tartrate.

Cholinesterase Deactivator: Obidoxime Chloride; Pralidoxime Chloride; Pralidoxime Iodide; Pralidoxime Mesylate.

Coccidiostat: Arprinocid; Narasin; Semduramicin; Semduramicin Sodium.

Cognition adjuvant: Ergoloid Mesylates; Piracetam; Pramiracetam Hydrochloride; Pramiracetam Sulfate; Tacrine Hydrochloride.

Cognition enhancer: Besipirdine Hydrochloride; Linopirdine; Sibopirdine.

Depressant: Omeprazole.

Diagnostic aid: Aminohippurate Sodium; Anazolene Sodium; Arclofenin; Arginine; Bentiromide; Benzylpenicilloyl Polylysine; Butedronate Tetrasodium; Butilfenin; Coccidioidin; Corticorelin Ovine Triflutate; Corticotropin, Repository; Corticotropin Zinc Hydroxide; Diatrizoate Meglumine; Diatrizoate Sodium; Diatrizoic Acid; Diphtheria Toxin for Schick Test; Disofenin; Edrophonium Chloride; Ethiodized Oil; Etifenin; Exametazime; Ferristenc; Ferumoxides; Ferumoxsil; Fluorescein; Fluorescein Sodium; Gadobenate Dimeglumine; Gadoteridol; Gadodiamide; Gadopentetate Dimeglumine; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Ioglicic Acid; Ioglicic Acid; Ioglucol; Ioglucomide; Ioglycamic Acid; Iogulamide; Iohexol; Iomeprol; Iopamidol; Iopanoic Acid; Iopentol; Iophendylate; Iprofenin; Iopronic Acid; Ioprocemic Acid; Iopydol; Iopydone; Iosefamic Acid; Ioseric Acid; Iosulamide Meglumine; Iosulmetic Acid; Iotasul; Iotetric Acid; Iothalamate Meglumine; Iothalamate Sodium; Iothalamic Acid; Iotrolan; Iotroxic Acid; Ioversol; Ioxaglate Meglumine; Ioxagiate Sodium; Ioxaglic Acid; Ioxilan; Ioxotrizoic Acid; Ipodate Calcium; Ipodate Sodium; Isosulfan Blue; Leukocyte Typing Serum; Lidofenin; Mebrofenin; Meglumine; Metrizamide; Metrizoate Sodium; Metyrapone; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; Tyropanoate Sodium; Xylose.

Diuretic: Ambuphylline; Ambuside; Amiloride Hydrochloride; Azolimine; Azosemide; Brocrinat; Bumetanide; Chlorothiazide; Chlorthalidone; Clazolimine; Clorexolone; Ethacrynate Sodium; Ethacrynic Acid; Etozolin; Fenquizone; Furosemide; Hydrochlorothiazide; Isosorbide; Mannitol; Mefruside; Ozolinone; Piretanide; Spiroxasone; Torsemide; Triamterene; Triflocin; Urea.

Dopaminergic agent: Ibopamine.

Ectoparasiticide: Nifluridide; Permethrin.

Emetic: Apomorphine Hydrochloride.

Enzyme inhibitor: Acetohydroxamic Acid; Alrestatin Sodium; Aprotinin; Benazepril Hydrochloride; Benazeprilat; Benurestat; Bromocriptine; Bromocriptine Mesylate; Cilastatin Sodium; Flurofamide; Lergotrile; Lergotrile Mesylate; Levcycloserine; Libenzapril; Pentopril; Pepstatin; Perindopril; Polignate Sodium; Sodium Amylosulfate; Sorbinil; Spirapril Hydrochloride; Spiraprilat; Taleranol; Teprotide; Tolfamide; Zofenopril Calcium.

Estrogen: Chlorotrianisene; Dienestrol; Diethylstilbestrol; Diethylstilbestrol Diphosphate; Equilin; Estradiol; Estradiol Cypionate; Estradiol Enanthate; Estradiol Undecylate; Estradiol Valerate; Estrazinol Hydrobromide; Estriol; Estrofurate; Estrogens, Conjugated; Estrogens, Esterified; Estrone; Estropipate; Ethinyl Estradiol; Fenestrel; Mestranol; Nylestriol; Quinestrol.

Fibrinolytic: Anistreplase; Bisobrin Lactate; Brinolase.

Free oxygen radical scavenger: Pegorgotein.

Gastrointestinal Motility agents: Cisapride (Propulsid); Metoclopramide (Reglan); Hyoscyamine (Levsin).

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Corticotropin, Repository; Corticotropin Zinc Hydroxide; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Phosphate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; Triamcinolone Hexacetonide.

Gonad-stimulating principle: Buserelin Acetate; Clomiphene Citrate; Ganirelix Acetate; Gonadorelin Acetate; Gonadorelin Hydrochloride; Gonadotropin, Chorionic; Menotropins.

Hair growth stimulant: Minoxidil.

Hemostatic: Aminocaproic Acid; Oxamarin Hydrochloride; Sulmarin; Thrombin; Tranexamic Acid.

Histamine H2 receptor antagonists: Ranitidine (Zantac); Famotidine (Pepcid); Cimetidine (Tagamet); Nizatidine (Axid).

Hormone: Diethylstilbestrol; Progesterone; 17 hydroxy progesterone; Medroxyprogesterone; Norgestrel; Norethynodrel; Estradiol; Megestrol (Megace); Norethindrone; Levonorgestrel; Ethyndiol; Ethinyl estradiol; Mestranol; Estrone; Equilin; 17 alpha dihydroequilin; equilenin; 17 alpha dihydroequilenin; 17 alpha estradiol; 17 beta estradiol; Leuprolide (lupron); Glucagon; Testolactone; Clomiphene; Han memopausal gonadotropins; Human chorionic gonadotropin; Urofollitropin; Bromocriptine; Gonadorelin; Luteinizing hormone releasing hormone and analogs; Gonadotropins; Danazol; Testosterone; Dehydroepiandrosterone; Androstenedione; Dihydroestosterone; Relaxin; Oxytocin; Vasopressin; Folliculostatin; Follicle regulatory protein; Gonadoctrinins; Oocyte maturation inhibitor; Insulin growth factor; Follicle Stimulating Hormone; Luteinizing hormone; Tamoxifen.; Corticorelin Ovine Triffutate; Cosyntropin; Metogest; Pituitary, Posterior; Seractide Acetate; Somalapor; Somatrem; Somatropin; Somenopor; Somidobove.

Hypocholesterolemic: Lifibrol.

Hypoglycemic: Darglitazone Sodium: Glimepiride.

Hypolipidemic: Azalanstat Dihydrochloride; Colestolone; Surfomer; Xenalipin.

Hypotensive: Viprostol.

HMGCoA reductase inhibitors: Lovastatin (Mevacor); Simvastatin (Zocor); Pravastatin (Pravachol); Fluvastatin (Lescol).

Immunizing agent: Antirabies Serum; Antivenin (Latrodectus mactans); Antivenin (Micrurus Fulvius); Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; $Rh_o(D)$ Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Yellow Fever vaccine; Vaccinia Immune Globulin; Varicella-Zoster Immune Globulin.

Immunomodulator: Dimepranol Acedoben; Imiquimod; Interferon Beta-1b; Lisofylline; Mycophenolate Mofetil; Prczatide Copper Acetate.

Immunoregulator: Azarole; Fanetizole Mesylate; Frentizole; Oxamisole Hydrochloride; Ristianol Phosphate; Thymopentin; Tilomisole.

Immunostimulant: Loxoribine; Teceleukin.

Immunosuppressant: Azathioprine; Azathioprine Sodium; Cyclosporine; Daltroban; Gusperimus Trihydrochloride; Sirolimus; Tacrolimus.

Impotence therapy adjunct: Delequamine Hydrochloride.

Inhibitor: Acarbose; Atorvastatin Calcium; Benserazide; Brocresine; Carbidopa; Clavulanate Potassium; Dazmegrel; Docebenone; Epoprostenol; Epoprostenol Sodium; Epristeride; Finasteride; Flurbiprofen Sodium; Furegrelate Sodium; Lufironil; Miglitol; Orlistat; Pimagedine Hydrochloride; Pirmagrel; Ponalrestat; Ridogrel; Sulbactam Benzathine; Sulbactarn Pivoxil; Sulbactam Sodium; Suronacrine Maleate; Tazobactam; Tazobactam Sodium; Ticlopidine Hydrochloride; Tirilazad Mesylate; Tolrestat; Velnacrine Maleate; Zifrosilone; Zileuton.

Keratolytic: Alcloxa; Aldioxa; Benzoyl Peroxide; Dibenzothiophene; Etarotene; Isotretinoin; Motretinide; Picotrin Diolamine; Resorcinol; Resorcinol Monoacetate; Salicylic Acid; Sumarotene; Tazarotene; Tetroquinone; Tretinoin.

LHRH agonist: Deslorelin; Goserelin; Histrelin; Lutrelin Acetate; Nafarelin Acetate.

Liver disorder treatment: Malotilate.

Luteolysin: Fenprostalene.

Memory adjuvant: Dimoxamine Hydrochloride; Ribaminol.

Mental performance enhancer: Aniracetam.

Mood regulator: Fengabine.

Mucolytic: Acetylcysteine; Carbocysteine; Dormiodol.

Mucosal Protective agents: Misoprostol (Cytotec).

Mydriatic: Berefrine.

Nasal decongestant: Nemazoline Hydrochloride; Pseudoephedrine Polistirex.

Neuroleptic: Duoperone Fumarate; Risperidone.

Neuromuscular blocking agent: Atracurium Besylate; Cisatracurium Besylate; Doxacurium Chloride; Gallamine Triethiodide; Metocurine Iodide; Mivacurium Chloride; Pancuronium Bromide; Pipecuronium Bromide; Rocuronium Bromide; Succinylcholine Chloride; Tubocurarine Chloride; Vecuronium Bromide.

Neuroprotective: Dizocilpine Maleate.

NMDA antagonist: Selfotel.

Non-hormonal sterol derivative: Pregnenolone Succinate.

Oxytocic: Carboprost; Carboprost Methyl; Carboprost Tromethamine; Dinoprost; Dinoprost Tromethamine; Dinoprostone; Ergonovine Maleate; Meteneprost; Methylergonovine Maleate; Oxytocin; Sparteine Sulfate.

Plasminogen activator: Alteplase; Urokinase.

Platelet activating factor antagonist: Lexipafant.

Platelet aggregation inhibitor: Acadesine; Beraprost; Beraprost Sodium; Ciprostene Calcium; Itazigrel; Lifarizine; Oxagrelate.

Post-stroke and post-head trauma treatment: Citicoline Sodium.

Potentiator: Pentostatin; Talopram Hydrochloride.

Progestin: Algestone Acetophenide; Amadinone Acetate; Anagestone Acetate; Chlormadinone Acetate; Cingestol; Clogestone Acetate; Clomegestone Acetate; Desogestrel; Dimethisterone; Dydrogesterone; Ethynerone; Ethynodiol Diacetate; Etonogestrel; Flurogestone Acetate; Gestaclone; Gestodene; Gestonorone Caproate; Gestrinone; Haloprogesterone; Hydroxyprogesterone Caproate; Levonorgestrel; Lynestrenol; Medrogestone; Medroxyprogesterone Acetate; Methynodiol Diacetate; Norethindrone; Norethindrone Acetate; Norethynodrel; Norgestimate; Norgestomet; Norgestrel; Oxogestone Phenpropionate; Progesterone; Quingestanol Acetate; Quingestrone; Tigestol.

Prostaglandin: Cloprostenol Sodium; Fluprostenol Sodium; Gemeprost; Prostalene; Sulprostone.

Prostate growth inhibitor: Pentomone.

Prothyrotropin: Protirelin.

Psychotropic: Minaprine.

Pulmonary surface: Beractant; Colfosceril Palmitate.

Radioactive agent: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131 Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iotalamate Sodium I 131; Iotyrosine 1 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine 1 125; Thyroxine 1 131; Tolpovidone 1 131; Triolein 1 125; Triolein 1 131.

Regulator: Calcifediol; Calcitonin; Calcitriol; Clodronic Acid; Dihydrotachysterol; Etidronic Acid; Oxidronic Acid; Piridronate Sodium; Risedronate Sodium; Secalciferol.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalamide; Fenyripol Hydrochloride; Fetoxylate Hydrochloride; Flavoxate Hydrochloride; Fletazepam; Flumetramide; Flurazepam Hydrochloride; Hexafluorenium Bromide; Isomylamine Hydrochloride; Lorbamate; Mebeverine Hydrochloride; Mesuprine Hydrochloride; Metaxalone; Methocarbamol; Methixene Hydrochloride; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; Xilobam.

Repartitioning agent: Cimaterol.

Scabicide: Amitraz; Crotamiton.

Sclerosing agent: Ethanolamine Oleate; Morrhuate Sodium; Tribenoside.

Sedative: Propiomazine.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam; Ethchlorvynol; Etomidate; Fenobam; Flunitrazepam; Fosazepam; Glutethimide; Halazepam; Lormetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Thalidomide; Tracazolate; Trepipam Maleate; Triazolam; Tricetamide; Triclofos Sodium; Trimetozine; Uldazepam; Zaleplon; Zolazepam Hydrochloride; Zolpidem Tartrate.

Selective adenosine Al antagonist: Apaxifylline.

Serotonin antagonist: Altanserin Tartrate; Amesergide; Ketanserin; Ritanserin.

Serotonin inhibitor: Cinanserin Hydrochloride; Fenclonine; Fonazine Mesylate; Xylamidine Tosylate.

Serotonin receptor antagonist: Tropanserin Hydrochloride.

Steroid: Dexamethasone Acefurate; Mometasone Furoate.

Stimulant: Amfonelic Acid; Amphetamine Sulfate; Ampyzine Sulfate; Arbutamine Hydrochloride; Azabon; Caffeine; Ceruletide; Ceruletide Diethylamine; Cisapride; Dazopride Fumarate; Dextroamphetamine; Dextroamphetamine Sulfate; Difluanine Hydrochloride; Dimefline Hydrochloride; Doxapram Hydrochloride; Etryptamine Acetate; Ethamivan; Fenethylline Hydrochloride; Flubanilate Hydrochloride; Flurothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; Xamoterol Fumarate.

Suppressant: Amflutizole; Colchicine; Tazofelone.

Symptomatic multiple sclerosis: Fampridine.

Synergist: Proadifen Hydrochloride.

Thyroid hormone: Levothyroxine Sodium; Liothyronine Sodium; Liotrix.

Thyroid inhibitor: Methimazole; Propylthiouracil.

Thyromimetic: Thyromedan Hydrochloride.

Tranquilizer: Bromazepam; Buspirone Hydrochloride; Chlordiazepoxide; Clazolam; Clobazam; Clorazepate Dipotassium; Clorazepate Monopotassium; Demoxepam; Dexmedetomidine; Enciprazine Hydrochloride; Gepirone Hydrochloride; Hydroxyphenamate; Hydroxyzine Hydrochloride; Hydroxyzine Pamoate; Ketazolam; Lorazepam; Lorzafone; Loxapine; Loxapine Succinate; Medazepam Hydrochloride; Nabilone; Nisobamate; Oxazepam; Pentabamate; Pirenperone; Ripazepam; Rolipram; Sulazepam; Taciamine Hydrochloride; Temazepam; Triflubazam; Tybamate; Valnoctamide.

Amyotrophic lateral sclerosis agents: Riluzole.

Cerebral ischemia agents: Dextrorphan Hydrochloride.

Paget's disease agents: Tiludronate Disodium.

Unstable angina agents: Tirofiban Hydrochloride.

Uricosuric: Benzbromarone; Irtemazole; Probenecid; Sulfinpyrazone.

Vasoconstrictor: Angiotensin Amide; Felypressin; Methysergide; Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Diltiazem Hydrochloride; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nifedipine; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; Xanthinol Niacinate.

Vulnerary: Allantoin.

Wound healing agent: Ersofermin.

Xanthine oxidase inhibitor: Allopurinol; Oxypurinol

Other pharmaceutical agents include: 1-decpyrrolidinone; 1-dodecpyrrolidinone; 16-alpha fluoroestradiol;

16-epiestriol; 16alpha-gitoxin; 17alpha estradiol; 17beta estradiol; 1alpha-hydroxyvitamin D2; 2'-nor-cGMP; 20-epi-1,25 dihydroxyvitamin D3; 22-oxacalcitriol; 2CVV; 3-isobutyl GABA; 6-FUDCA; 7-methoxytacrine; abamectin; abanoquil; abecarnil; abiraterone; acadesine; acamprosate; acarbose; aceclofenac; acemannan; acetomepregenol; acetyl-L-carnitine; acetylcysteine, N-; acetylmethadol; acifran; acipimox; acitemate; acitretin; aclarubicin; aclatonium; napadisilate; aconiazide; acrivastinet; adafenoxate; adapalene; adatanserin; adecypenol; adefovir dipivoxil; adelmidrol; ademetionine; adinazolam; adiposin; adozelesin; adrafinil; alacepril; aladapcin; alaptide; albendazole; albolabrin; aldecalmycin; aldesleukin; alendronic acid; alentemol; alfacalcidol; alfuzosin; alglucerase; alinastine; alosetron; alpha idosone; alprostadil; altretamine; altromycin B; ambamustine; amelometasone; amesergide; amezinium metilsulfate; amfebutamone; amidox; amifloxacin; amifostine; amiodarone; amisulpride; amlexanox; amlodipine; amlodipine; ampiroxicam; amrinone; amrubicin; amsacrine; amylin; amythiamicin; anagrelide; anakinra; ananain; anaritide; anastrozole; andrographolide; anordrin; apadoline; apafant; apaxifylline; aphidicolin glycinate; apraclonidine; aprosulate sodium; aptiganel; apurinic acid; aranidipine; arbekacin; arbidol; arbutamine; ardeparin sodium; arecatannin B1; argatroban; aripiprazol; arotinolol; asimadoline; aspalatone; asperfuran; aspoxicillin; astemizole; asulacrine; atamestane; atenolol, S—; atevirdine; atosiban; atovaquone; atpenin B; atrimustine; atrinositol; aureobasidin A; azadirachtine; azasetron; azatyrosine; azelaic acid; azelastine; azelnidipine; azimilide; azithromycin; azosemide; aztreonam; baccatin III; bacoside A; bacoside B; bactobolamine; balazipone; balhimycin; balofloxacin; balsalazide; bambuterol; baohuoside 1; barnidipine; basifungin; batebulast; batimastat; beauvericin; becaplermin; becliconazole; befloxatone; belfosdil; bellenamine; benflumetol; benidipine; benzisoxazole; benzochlorins; benzoidazoxan; benzoylstaurosporine; benztropine; bepridil; beractant; beraprost; berlafenone; bertosamil; besipirdine; beta-alethine; betaclamycin B; betamipron; betaxolol; betulinic acid; bevantolol; bicalutamide; bifemelane; bimakalim; bimithil; binospirone; bioxalomycin alpha2; biriperone; bis-benzimidazole A; bis-benzimidazole B; bisantrene; bisaramil; bisaziridinylspermine; bisnafide; bisoprolol; bistramide D; bistramide K; bistratene A; boldine; bopindolol; brefeldin; breflate; brimonidine; bromfenac; bromperidol; bropirimine; bucindolol; budesonide; budipine; budotitane; bunaprolast; bunazosin; butenafine; buthionine sulfoximine; butixocort propionate; cadexomer iodine; calanolide A; calcipotriol; calphostin C; camonagrel; candesartan; candesartan cilexetil; candoxatril; candoxatrilat; capecitabine; capromab; capsaicin; captopril; carbazomycin C; carbetocin; carbovir; carboxamide-amino-triazole; carboxyamidotriazole; carboxymethylated beta-1,3-glucan; carperitide; carteolol; carumonam; carvedilol; carvotroline; carzelesin; castanospermine; cebaracetam; cecropin B; cefcapene pivoxil; cefdaloxime pentexil tosilate; cefdinir; cefditoren pivoxil; cefepime; cefetamet; cefetamet pivoxil; cefixime; cefluprenam; cefmetazole; cefminox; cefodizime; cefoselis; cefotetan; cefotiam; cefotiam hexetil; cefozopran; cefpimizole; cefpiramide; cefpirome; cefpodoxime proxetil; cefprozil; cefsulodin; cefteram; ceftibuten; ceftriaxone; cefuroxime axetil; celastrol; celikalim; celiprolol; cepacidine A; cericlamine; cerivastatin; ceronapril; certoparin sodium; cetiedil; cetirizine; chloroorienticin A; chloroorienticin B; chloroquinoxaline sulfonamide; cibenzoline; cicaprost; ciclesonide; cicletanine; cicloprolol; cidofovir; cilansetron; cilazapril; cilnidipine; cilobradine; cilostazol; cimetropium bromide; cinitapride; cinolazepam; cioteronel; ciprofibrate; ciprofloxacin; ciprostene; cis-porphyrin; cisapride; cisatracurium besilate; cistinexine; citalopram; citicoline; citreamicin alpha; cladribine; clarithromycin; clausenamide; clebopride; clinafloxacin; clobazam; clobetasone butyrate; clodronic acid; clomethiazole; clopidogrel; clotrimazole; colestimide; colfosceril palmitate; collismycin A; collismycin B; combretastatin A4; complestatin; conagenin; contignasterol; contortrostatin; cosalane; costatolide; cotinine; coumermycin A1; cucumariosid; curacin A; curdlan sulfate; curiosin; cyclazosin; cyclic HPMPC; cyclobenzaprine; cyclobut A; cyclobut G; cyclocapron; cycloplatam; cyclosin; cyclothialidine; cyclothiazomycin; cypemycin; cyproterone; cytarabine ocfosfate; cytochalasin B; daclizimab; dactimicin; daidzein; daidzin; dalfopristin; dalteparin sodium; danaparoid; daphnodorin A; dapiprazole; dapitant; darifenacin; darlucin A; darsidomine; ddUTP; decitabine; deferiprone; deflazacort; dehydrodiderniin B; dehydroepiandrosterone; Delapril; delequamine; delfaprazine; delmopinol; delphinidin; deoxypyridinoline; deprodone; depsidomycin; deramciclane; dermatan sulfate; desflurane; desirudin; deslorelin; desmopressin; desogestrel; desoxoamiodarone; detajmium bitartrate; dexifosfamide; dexketoprofen; dexloxiglumide; dexmedetomidine; dexpemedolac; dexrazoxane; dexsotalol; dextrin 2-sulphate; dexverapamil; dezinamide; dezocine; diaziquone; diclofenac digolil; diclofenac potassium; dicranin; didemnin B; didox; dienogest; diethylhomospermine; diethylnorspermine; dihydrexidine; dihydro-5-azacytidine; dimethyl prostaglandin A1; dimethylhomospermine; dimiracetam; dioxamycin; diphencyprone; diphenyl spiromustine; diprafenone; dipropylnorspermine; dirithromycin; discodermolide; disulfiram; ditekiren; docarpamine; docosanol, 1-; dofetilide; dolasetron; domitroban; dopexamine; dorzolamide; dosmalfate; dotarizine; doxacurium chloride; doxazosin; doxifluridine; doxofylline; draculin; draflazine; droloxifene; dronabinol; drosperidone; drotaverine acephyllinate; droxicam; ebiratide; ebrotidine; ebselen; ecabapide; ecabet; ecadotril; ecdisteron; echicetin; echistatin; ecomustine; ecteinascidin 722; ecteinascidin 729; ecteinascidin 743; edaravone; edelfosine; edobacomab; edrecolomab; efegatran; eflornithine; efonidipine; egualen; elcatonin; eletriptan; elgodipine; eliprodil; eltenac; emlkalim; emedastine; emiglitate; emitefur; emoctakin; enadoline hydrochloride; enalapril; enazadrem; englitazone; enlimomab; enoxacin; enoxaparin sodium; enoximone; entacapone; enterostatin; epoprostenol; epoxymexrenone; epristeride; eprosartan; eptastigmine; erdosteine; ersentilide; ersofermin; erythiritol; esuprone; etanidazole; etanterol; ethacizin; ethinylestradiol; etizolam; etodolac; etoposide phosphate; etrabamine; everninomicin; examorelin; exemestane; fadrozole; faeriefungin; famciclovir; fampridine; fantofarone; faropenem; fasidotril; fasudil; fazarabine; fedotozine; felbamate; fenofibrate; fenoldopam; fenretinide; fenspiride; fenticonazole; fepradinol; ferpifosate sodium; ferristene; ferrixan; ferumoxsil; fexofenadine; flavopiridol; flecainide; flerobuterol; fleroxacin; flesinoxan; flezelastine; flobufen; flomoxef; florfenicol; florifenine; flosatidil; fluasterone; fluconazole; fludarabine; flumazenil; flumecinol; flumequine; flunarizine; fluocalcitriol; fluorodaunorunicin hydrochloride; fluoxetine, R-; fluoxetine, S-; fluparoxan; flupirtine;

flurbiprofen axetil; flurithromycin; fluticasone propionate; flutrimazole; fluvastatin; fluvoxamine; forasartan; forfenimex; formestane; formoterol; formoterol, R,R-; fosfomycin; trometamol; fosinopril; fosphenytoin; fostriecin; fotemustine; gabapentin; gadobenic acid; gadobutrol; gadodiamide; gadodiamide-EOB-DTPA; gadolinium texaphyrin; gadoteric acid; gadoteridol; gadoversetamide; galantamine; galdansetron; gallopamil; galocitabine; gamolenic acid; ganirelix; gepirone; gestrinone; girisopam; glaspimod; glaucocalyxin A; glutapyrone; glycopine; glycopril; granisetron; grepafloxacin; halichondrin B; halofantrine; halomon; halopredone; hatomamicin; hatomarubigin A; hatomarubigin B; hatomarubigin C; hatomarubigin D; ibogaine; ibopamine; ibudilast; illimaquinone; ilmofosine; ilomastat; iloperidone; iloprost; imidapril; imidazenil; indinavir; indolidan; indometacin farnesil; indometacin; tropine ester; indoramin; inocoterone; inogatran; inolimomab; interferon alfa; interferon alfa-2a; interferon alfa-2b; interferon alfa-N 1; interferon alfa-n3; interferon beta; interferon beta-1a1; interferon beta-1b; interferon gamma-1a; interferon gamma-1b; interferon omega; interferon, consensus; interleukin-1; interleukin-1 alpha; interleukin-beta; interleukin-10; interleukin-1 1; interleukin-12; interleukin-12; interleukin-15; interleukin-2; interleukin-3; interleukin-4; interleukin-5; interleukin-7; interleukin-8; iobenguane; iobitridol; iodoamiloride; iododoxorubicin; iofratol; iomeprol; iopentol; iopromide; iopyrol; iotriside; ioversol; ioxilan; ipazilide; IpdR; ipenoxazone; ipidacrine; ipomeanol, 4-; ipriflavone; ipsapirone; irbesartan; irinotecan; irloxacin; irsogladine; irtemazole; isalsteine; isbogrel; isepamicin; isobengazole; isofloxythepin; isohomohalicondrin B; isopropyl unoprostone; isradipine; itameline; itasetron; itopride; itraconazole; ketoprofen, R-; ketoprofen, S-; ketorolac; lacidipine; lactitol; lactivicin; laennec; lafutidine; lamellarin-N triacetate; lamifiban; lamivudine; lamotrigine; lanoconazole; lanperisone; lanreotide; lansoprazole; latanoprost; lateritin; laurocapram; lazabemide; lemefloxacin; lemildipine; leminoprazole; lenercept; lenograstim; lentinan sulfate; leptin; leptolstatin; lercanidipine; lerisetron; lesopitron; letrazuril; letrozole; leucomyzin; leuprorelin; levcromakalim; levetiracetam; levobetaxolol; levobunolol; levobupivacaine; levocabastine; levocarnitine; levodropropizine; levofloxacin; levomoprolol; levonorgestrel; levormeloxifene; levosimendan; levosulpiride; linotroban; linsidomine; lintitript; lintopride; liothyronine sodium; lirexapride; lisinopril; lobaplatin; lobucavir; lodoxamide; lombricine; lomefloxacin; lomerizine; lometrexol; lonazolac; lonidamine; loracarbef; loratadine; lorglumide; lomoxicam; losartan; losigamone; losoxantrone; loteprednol; loviride; loxoribine; lubeluzole; lurtotecan; luteinizing hormone; lutetium; luzindole; lydicamycin; lysofylline; lysostaphin; magainin 2 amide; magnolol; mallotochromene; mallotojaponin; malotilate; mangafodipir; manidipine; maniwamycin A; mannostatin A; manumycin E; manumycin F; mapinastine; marimastat; Martek 8708; Martek 92211; masoprocol; maspin; massetolide; meterelin; methoxatone; methylhistamine, R-alpha; methylinosine monophosphate; methylprednisolone aceponate; methylprednisolone suleptanate; metipamide; metoclopramide; metoprolol, S-; metrifonate; mibefradil; michellamine B; microcolin A; midodrine; mifepristone; miglitol; milacemide; milameline; mildronate; milnacipran; milrinone; miltefosine; minaprine; miokamycin; mipragoside; mirfentanil; mirimostim; mirtazapine; misoprostol; mitoguazone; mitolactol; mitonafide; mitoxantrone; mivacurium chloride; mivazerol; mixanpril; mizolastine; mizoribine; moclobemide; modafinil; moexipril; mofarotene; mofezolac; molgramostim; mometasone; montirelin; mopidamol; moracizine; mosapramine; mosapride; motilide; moxiraprine; moxonidine; nadifloxacin; nadroparin calcium; nafadotride; nafamostat; nafarelin; naftopidil; naglivan; nagrestip; nalmefene; naphterpin; napsagatran; naratriptan; nartograstim; nasaruplase; nateplase; niperotidine; niravoline; nisamycin; nisin; nisoldipine; nitazoxanide; nitecapone; nitrendipine; nitrendipine, S-; nitrofurantoin monohydrate; nitrullyn; nizatidine; ofloxacin; okicenone; olanzapine; olopatadine; olprinone; olsalazine; omeprazole; onapristone; ondansetron; ondansetron, R-; ontazolast; oracin; otenzepad; oxaliplatin; oxamisole, oxandrolone; oxaprozin; oxaunomycin; oxcarbazepine; oxiconazole; oxiracetam; oxodipine; ozagrel; palauamine; palinavir; palmitoylrhizoxin; pamaqueside; pamicogrel; pamidronic acid; panamesine; panaxytriol; panipenem; panipenum; pannorin; panomifene; pantethine; pantoprazole; parabactin; pamaparin sodium; paroxetine; parthenolide; pazelliptine; pazufloxacin; pefloxacin; pegaspargase; peldesine; pemedolac; pemirolast; penciclovir; pentafuside; pentamidine; pentamorphone; pentigetide; pentosan; pentostatin; pentrozole; perflubron; perfosfamide; pergolide; perindoprilat; perospirone; phenaridine; phenazinomycin; phenserine; phensuccinal; phentolamine mesilate; phenylacetate; phenylalanyl ketoconazole; picenadol; picibanil; picroliv; picumeterol; pidotimod; pilocarpine hydrochloride; pilsicainide; pimagedine; pimilprost; pimobendan; pinacidil; pinocebrin; pioglitazone; pipecuronium bromide; pirarubicin; piretanide; pirfenidone; piritrexim; pirlindole; pirmagrel; pirmenol; pirodavir; pirodomast; piroxicam cinnamate; propagermanium; propentofylline; propionylcarnitine, L-; propiram; propiram+paracetamol; propiverine; propyl bis-acridone; prostaglandin J2; prostratin; protegrin; protosufloxacin; prulifloxacin; pyrazoloacridine; quazepam; quetiapine; quiflapon; quinagolide; quinapril; quinfamide; quinupristin; raloxifene; raltitrexed; ramatroban; ramipril; ramosetron; ranelic acid; ranitidine bismuth citrate; ranolazine; recainam; regavirumab; relaxin; repirinast; resinferatoxin; reticulon; reviparin sodium; revizinone; ricasetron; ridogrel; rifabutin; rifapentine; rifaximin; rilopirox; riluzole; rimantadine; rimexolone; rimoprogin; riodipine; ripisartan; risedronic acid; rispenzepine; risperidone; ritanserin; ritipenem; ritipenem acoxil; ritolukast; ritonavir; rizatriptan benzoate; rohitukine; rokitamycin; ropinirole; ropivacaine; roquinimex; roxatidine; roxindole; roxithromycin; rubiginone B1; ruboxyl; rufloxacin; rupatidine; ruzadolane; safingol; safironil; saintopin; salbutamol, R-; salmeterol; salmeterol, R-salnacedin; sameridine; sampatrilat; sanfetrinem; saprisartan; sapropterin; saquinavir; SarCNU; sarcophytol A sargramostim; sarpogrelate; saruplase; saterinone; satigrel; satumomab pendetide; selegiline; selenium thiosemicarbazone; sematilide; semduramicin; semotiadil; semustine; sermorelin; sertaconazole; sertindole; sertraline; setiptiline; sevirumab; sevoflurane; sezolamide; silipide; silteplase; simendan; simvastatin; sinitrodil; sinnabidol; sipatrigine; sirolimus; sizofiran; somatomedin B; somatomedin C; somatrem; somatropin; sonermin; sotalol; staurosporine; stavudine; stepronin; stipiamide; stiripentol; stobadine; succibun; sucralfate; sulfasalazine; sulfmosine; sulfoxamine; sulopenem; sultamicillin; sultopride; sulukast; sumatriptan; symakalim; tandospirone; tapgen; taprostene; tasosartan; tazanolast;

tazarotene; teicoplanin; telenzepine; tellurapyrylium; telmesteine; telmisartan; temocapril; temoporfin; temozolomide; tenidap; teniposide; tenosal; tenoxicam; tepirindole; tepoxalin; terazosin; terbinafine; terfenadine; terflavoxate; terguride; terlakiren; terlipressin; terodiline; tertatolol; testosterone buciclate; tetrachlorodecaoxide; tetrazomine; thaliblastine; thalidomide; thiocoraline; thiofedrine; thiomarinol; thioperamide; thyroid stimulating hormone; tiagabine; tianeptine; tiapafant; tibolone; ticlopidine; tienoxolol; tilisolol; tilnoprofen arbamel; tiludronic acid; tinzaparin sodium; tiotropium bromide; tipredane; tiqueside; tirandalydigin; tirapazamine; tirilazad; tirofiban; tiropramide; topsentin; torasemide; toremifene; tosufloxacin; trafermin; trandolapril; traxanox; tretinoin; tretinoin tocoferil; triacetyluridine; tricaprilin; trichohyalin; trichosanthin, alpha; triciribine; trientine; triflavin; trimegestone; triptorelin; troglitazone; trombodipine; tropisetron; trospectomycin; trovafloxacin; trovirdine; tucaresol; tulobuterol; tylogenin; urapidil; uridine triphosphate; valaciclovir; valproate magnesium; valproate semisodium; valsartan; vamicamide; vanadeine; vaninolol; vapreotide; variolin B; velaresol; venlafaxine; veramine; verapamil, (S); verdins; veroxan; verteporfin; vesnarinone; vexibinol; vigabatrin; vinburnine citrate; vinburnine resinate; vinconate; vinorelbine; vinpocetine; vinpocetine citrate; vintoperol; vinxaltine; voriconazole; vorozole; voxergolide; xemilofiban; ximoprofen; yangambin; zabicipril; zacopride; zacopride, R-; zafirlukast; zalcitabine; zaleplon; zalospirone; zaltoprofen; zanamivir; zankiren; zanoterone; zatebradine; zatosetron; zenarestat; zeniplatin; zifrosilone; zilascorb; zileuton; zinostatin stimalamer; ziprasidone; zoledronic acid; zolmitriptan; zolpidem; zonisamide; zopiclonre; zopiclone, S—; zopolrestat; zotepine.

The invention also embraces novel compositions of matter that are covalent conjugates of DHA and pharmaceutical agents that are noncentral nervous system active agents. Noncentral nervous system active agents have no function or use within the central nervous system. Their only use is outside of the central nervous system. Such agents include all drugs within certain of the foregoing categories and only some drugs within other of the foregoing catagories. For example, the entire catagory of blood glucose regulators have no use or function within the central nervous system. In contrast, certain anti-cancer agents are useful in the central nervous system whereas others are not. For example, central nervous system cancers are not hormone dependent, and, therefore, an anti-cancer agent such as Tamoxifen which treats certain hormone dependent cancers is not useful in the central nervous system. Those skilled in the art will be able to identify readily those catagories and/or members of a catagory which are noncentral nervous system active agents. Among the foregoing compounds, the following catagories and/or members of the following catagories are noncentral nervous system active agents: adrenocortical steroid; adrenocortical suppressant; aldosterone antagonist; amino acid; anabolic; androgen; antagonist; anthelmintic; anti-acne agent; anti-adrenergic; anti-allergic; anti-amebic; anti-androgen; anti-anemic; anti-anginal; anti-arthritic; anti-asthmatic; anti-atherosclerotic; antibacterial; anticholelithic; anticholelithogenic; anticholinergic; anticoagulant; anticoccidal; antidiabetic; antidiarrheal; antidiuretic; antidote; antiestrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimitotic; antimycotic, antineoplastic, antineutropenic, antiparasitic; antiperistaltic, antipneumocystic; antiproliferative; antiprostatic hypertrophy; antiprotozoal; antipruritic; antipsoriatic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; diagnostic aid; diuretic; ectoparasiticide; enzyme inhibitor; estrogen; fibrinolytic; free oxygen radical scavenger; glucocorticoid; gonad-stimulating principle; hair growth stimulant; hemostatic; hormone; hypocholesterolemic; hypoglycemic; hypolipidemic; hypotensive; immunizing agent; immunomodulator; immunoregulator; immunostimulant; immunosuppressant; impotence therapy adjunct; inhibitor; keratolytic; LHRH agonist; liver disorder treatment, luteolysin; mucolytic; mydriatic; nasal decongestant; neuromuscular blocking agent; non-hormonal sterol derivative; oxytocic; plasminogen activator; platelet activating factor antagonist; platelet aggregation inhibitor; potentiator; progestin; prostaglandin; prostate growth inhibitor; prothyrotropin; pulmonary surface; radioactive agent; regulator; relaxant; repartitioning agent; scabicide; sclerosing agent; selective adenosine Al antagonist; steroid; suppressant; symptomatic multiple sclerosis; synergist; thyroid hormone: thyroid inhibitor; thyromimetic; amyotrophic lateral sclerosis agents; Paget's disease agents; unstable angina agents; uricosuric; vasoconstrictor; vasodilator; vulnerary; wound healing agent; xanthine oxidase inhibitor.

As used herein, a taxane is a molecule that possesses the following tricyclic carbon-atom connectivity network, which may incorporate carbon-carbon multiple bonds, and which through the involvement of carbon-atom-noncarbon-atom bonds may include substituents, functional groups, and additional rings.

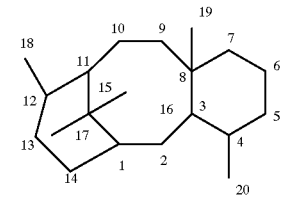

A taxoid is a molecule structurally related to a taxane in which the above taxane carbon-atom connectivity network is altered. for example, by cleavage of one or more of the carbocyclic rings, by deletion or addition of carbon substituents, by connection of carbon atoms normally not bonded to each other, by disconnection of carbon atoms normally bonded to each other, or by some other reorganization of or adjustment to the taxane carbon-atom connectivity network, but in which one or more structural features characteristic of the taxane carbon-atom connectivity network are conserved.

The compounds useful in the invention may be delivered in the form of anti-cancer cocktails. An anti-cancer cocktail is a mixture of any one of the compounds useful with this invention with another anti-cancer agent such as an anti-cancer drug, a cytokine, and/or supplementary potentiating agent(s). The use of cocktails in the treatment of cancer is routine. In this embodiment, a common administration vehicle (e.g., pill, tablet, implant, injectable solution, etc.)

would contain both the conjugate useful in this invention and the anti-cancer drug and/or supplementary potentiating agent.

The compounds of the invention, when used in cocktails, are administered in therapeutically effective amounts. A therapeutically effective amount will be determined by the parameters discussed below; but, in any event, is that amount which establishes a level of the drug(s) in the area of the tumor which is effective in inhibiting the tumor growth.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); boric acid and a salt (0.5–2.5% W/N); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods. Formulations for taxanes can be found in Chapter 9 of *Taxol: Science and Applications*, CRC Press, Inc., 2000 Corporate Boulevard, N.W., Boca Raton, Fla. 33431. In general, Taxol has been formulated as a 6 mg/ml cremophor EL (polyoxyethylated castor oil)/ethanol mixture, which is diluted to final volume with normal saline or 5% dextrose. A 15 mg/ml solution of taxotere has been formulated in polysorbate 80 (polyoxyethylene sorbitanmonooleate)/ethanol mixture, diluted with 5% dextrose.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa.

A subject as used herein means humans, primates, horses, cows, pigs, sheep, goats, dogs, cats and rodents.

The conjugates of the invention are administered in effective amounts. An effective amount means that amount necessary to delay the onset of, inhibit the progression of, halt altogether the onset or progression of or diagnose the particular condition being treated. In general, an effective amount for treating cancer will be that amount necessary to inhibit mammalian cancer cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m$^2$ per day will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day are contemplated to achieve appropriate systemic levels of compounds.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Intravenous routes are preferred.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

The conjugates of the invention also are useful, in general, for treating mammalian cell proliferative disorders other than cancer, including psoriasis, actinic keratosis, etc. They further are useful in treating diabetes and its complications, excess acid secretion, cardiovascular conditions involving cholesterol (e.g., hyperlipidemia and hypercholesterolemia), diarrhea, ovarian diseases (e.g. endometriosis, ovarian cysts, etc.) and as contraceptive agents.

Those skilled in the art will be able to recognize with no more than routine experimentation numerous equivalents to the specific products and processes described above. Such equivalents are intended to be included within the scope of the appended claims.

We claim as follows:

1. A method for targeting a drug to a noncentral nervous system tissue to treat a noncentral nervous system condition comprising:

administering to a subject in need of such treatment a covalent conjugate of cis-docosahexaenoic acid and a pharmaceutical agent effective for treating said noncentral nervous system condition, wherein the pharmaceutical agent is a noncentral nervous system acting agent that is nonactive within the central nervous system.

2. The method of claim 1, wherein the tissue is breast tissue and wherein the subject has a condition calling for treatment of breast tissue with the pharmaceutical agent.

3. The method of claim 1, wherein the tissue is gastrointestinal tissue and wherein the subject has a condition calling for treatment of gastrointestinal tissue with the pharmaceutical agent.

4. The method of claim 1, wherein the tissue is ovarian tissue and wherein the subject has a condition calling for treatment of ovarian tissue with the pharmaceutical agent.

5. The method of claim 1, wherein the pharmaceutical agent is a nonanti-cancer agent.

6. The method of claim 1, wherein the pharmaceutical agent is an anticancer agent.

7. A pharmaceutical preparation comprising:

a covalent conjugate of cis-docosahexanoic acid and a noncentral nervous system active agent, and a pharmaceutically acceptable carrier.

8. The pharmaceutical preparation as claimed in claim 7, wherein the noncentral nervous system active agent is active on a tissue selected from the group consisting of:

blood and blood forming tissue;

cardiovascular system tissue;

digestive and excretory system tissue;

endocrine system tissue;

musclar system tissue;

reproductive system tissue;

respiratory system tissue;

skeletal system tissue; and integumentary system tissue.

* * * * *

UNITED STATES PATENT AND TRADEMARK OFFICE
CERTIFICATE OF CORRECTION

PATENT NO. : 6,602,902 B2
DATED : August 5, 2003
INVENTOR(S) : Shashoua et al.

It is certified that error appears in the above-identified patent and that said Letters Patent is hereby corrected as shown below:

Column 52,
Line 24, replace "cis-docosahexanoic" with -- cis-docosahexaenoic --; and
Line 36, replace "musclar" with -- muscular --.

Signed and Sealed this

Second Day of March, 2004

JON W. DUDAS
*Acting Director of the United States Patent and Trademark Office*